US005751341A

United States Patent [19]
Chaleki et al.

[11] Patent Number: 5,751,341
[45] Date of Patent: *May 12, 1998

[54] STEREOSCOPIC ENDOSCOPE SYSTEM

[75] Inventors: Christopher R. Chaleki, Haydenville; Wayne P. Griffin, Dracut; E. Arthur Woodbury, Boxford; Arthur C. McKinley, Bradford; Harry R. McKinley, Southampton, all of Mass.

[73] Assignee: Vista Medical Technologies, Inc., Carlsbad, Calif.

[*] Notice: The term of this patent shall not extend beyond the expiration date of Pat. No. 5,538,497.

[21] Appl. No.: 720,816

[22] Filed: Oct. 2, 1996

Related U.S. Application Data

[63] Continuation of Ser. No. 227,675, Apr. 14, 1994, abandoned, which is a continuation-in-part of Ser. No. 76,944, Jun. 14, 1993, abandoned, and Ser. No. 664, Jan. 5, 1993, abandoned.

[51] Int. Cl.$^6$ .................................................. H04N 7/18
[52] U.S. Cl. ........................ 348/65; 348/45; 600/117
[58] Field of Search ........................ 348/65, 75, 42, 348/45; 356/241; 359/367; 396/17; 600/101, 117; H04N 7/18

[56] References Cited

U.S. PATENT DOCUMENTS

| Re. 33,854 | 3/1992 | Adair | 128/6 |
|---|---|---|---|
| 3,670,097 | 6/1972 | Jones | 178/6.5 |
| 4,281,341 | 7/1981 | Byatt | 348/57 |
| 4,310,849 | 1/1982 | Glass | 348/53 |
| 4,418,993 | 12/1983 | Lipton | 352/57 |
| 4,431,265 | 2/1984 | Benton | 350/132 |
| 4,472,037 | 9/1984 | Lipton | 352/57 |
| 4,480,263 | 10/1984 | van Merode | 348/60 |
| 4,523,226 | 6/1985 | Lipton et al. | 348/49 |
| 4,559,556 | 12/1985 | Wilkins | 348/58 |
| 4,562,463 | 12/1985 | Lipton | 348/56 |
| 4,582,396 | 4/1986 | Bos et al. | 350/347 E |

(List continued on next page.)

FOREIGN PATENT DOCUMENTS

| 0 463 723 | 5/1991 | European Pat. Off. | G02F 1/1335 |
|---|---|---|---|
| 2584599 | 1/1987 | France | G02B 23/26 |
| 63-149778 | 12/1989 | Japan | G02B 23/26 |
| 91/2709 | 1/1992 | South Africa | G02B 23/26 |
| WO91/00049 | 1/1991 | WIPO | A61B 1/04 |

OTHER PUBLICATIONS

International Search Report for PCT/US94/00116, mailed from EPO on Jun. 1, 1994, 7 pages.

PCT International Search Report for related international application No. PCT/US94/06673, 8 pages.

*Primary Examiner*—Howard W. Britton
*Assistant Examiner*—Vu Le
*Attorney, Agent, or Firm*—Pandiscio & Pandiscio

[57] ABSTRACT

A medical video endoscope system for allowing high-resolution three-dimensional images to be viewed has a stereoscopic endoscope for converting optical images of an object to left and right video image signals. An electronic processor module controls the stereoscopic endoscope and processes the left and right video image signals into time-multiplexed signals representative of high-resolution three-dimensional images having stereoscopic depth. The time-multiplexed signals are provided to a monitor which displays high-resolution video images based on the signals. A viewing device is provided which allows a viewer to see high-resolution three-dimensional video images having stereoscopic depth on the monitor. A rigid sheath assembly with an angled distal tip can be placed over a barrel of the endoscope and rotated with respect thereto in order to change the viewing direction of the stereoscopic endoscope. A conventional two-dimensional endoscope can be coupled to the three-dimensional medical video system by using a camera head designed to convert the two-dimensional optical images generated by the conventional endoscope into left and right signals which are then processed by the system as if they were received from a stereoscopic endoscope to create a two-dimensional video image.

31 Claims, 20 Drawing Sheets

U.S. PATENT DOCUMENTS

| | | | |
|---|---|---|---|
| 4,583,117 | 4/1986 | Lipton et al. | 348/47 |
| 4,588,259 | 5/1986 | Sheiman | 350/132 |
| 4,611,888 | 9/1986 | Prenovitz et al. | 348/75 |
| 4,651,201 | 3/1987 | Schoolman | 348/45 |
| 4,719,507 | 1/1988 | Bos | 348/57 |
| 4,736,246 | 4/1988 | Nishisawa | 348/56 |
| 4,792,850 | 12/1988 | Lipton et al. | 348/57 |
| 4,808,979 | 2/1989 | DeHoff et al. | 340/709 |
| 4,819,064 | 4/1989 | Diner | 348/47 |
| 4,851,901 | 7/1989 | Iwaski | 348/54 |
| 4,853,769 | 8/1989 | Kollin | 348/54 |
| 4,862,873 | 9/1989 | Yajima et al. | 128/6 |
| 4,870,600 | 9/1989 | Hiraoka | 364/522 |
| 4,873,572 | 10/1989 | Miyazaki et al. | 348/45 |
| 4,877,307 | 10/1989 | Kalmanash | 350/132 |
| 4,884,876 | 12/1989 | Lipton et al. | 350/347 E |
| 4,905,076 | 2/1990 | Annegarn et al. | 348/58 |
| 4,905,081 | 2/1990 | Morton | 348/43 |
| 4,907,860 | 3/1990 | Noble | 350/334 |
| 4,924,853 | 5/1990 | Jones, Jr. et al. | 128/6 |
| 4,926,257 | 5/1990 | Miyazaki | 348/45 |
| 4,941,457 | 7/1990 | Hasegawa | 128/6 |
| 4,943,852 | 7/1990 | Femano et al. | 348/49 |
| 4,954,890 | 9/1990 | Park | 348/58 |
| 4,967,268 | 10/1990 | Lipton et al. | 348/56 |
| 4,974,074 | 11/1990 | Tenma | 348/43 |
| 4,982,278 | 1/1991 | Dahl et al. | 348/53 |
| 5,001,555 | 3/1991 | Park | 348/43 |
| 5,003,385 | 3/1991 | Sudo | 348/49 |
| 5,007,715 | 4/1991 | Verhulst | 350/334 |
| 5,059,009 | 10/1991 | McKinley | 359/435 |
| 5,063,441 | 11/1991 | Lipton et al. | 348/47 |
| 5,065,236 | 11/1991 | Diner | 348/54 |
| 5,083,199 | 1/1992 | Börner | 348/59 |
| 5,084,763 | 1/1992 | Naradate et al. | 348/51 |
| 5,097,359 | 3/1992 | McKinley | 359/435 |
| 5,117,302 | 5/1992 | Lipton | 359/227 |
| 5,122,650 | 6/1992 | McKinley | 250/208.1 |
| 5,142,357 | 8/1992 | Lipton et al. | 348/48 |
| 5,166,787 | 11/1992 | Irion | 348/75 |
| 5,181,133 | 1/1993 | Lipton | 359/84 |
| 5,187,572 | 2/1993 | Nakamura et al. | 348/33 |
| 5,187,603 | 2/1993 | Bos | 359/73 |
| 5,188,634 | 2/1993 | Hussein et al. | 606/14 |
| 5,191,203 | 3/1993 | McKinley | 250/208.1 |
| 5,305,121 | 4/1994 | Moll | 348/65 |
| 5,538,497 | 7/1996 | Hori | 600/182 |
| 5,588,948 | 12/1996 | Takahashi et al. | 348/45 |

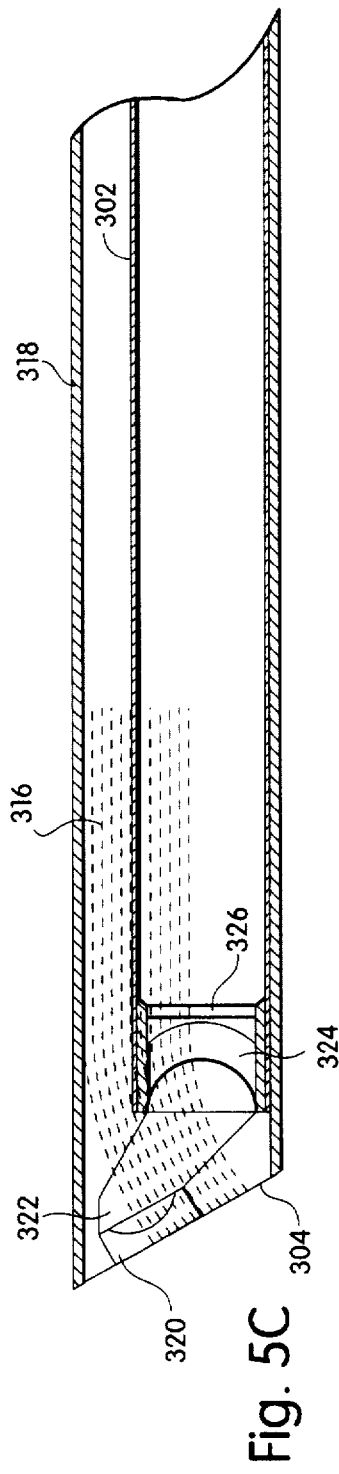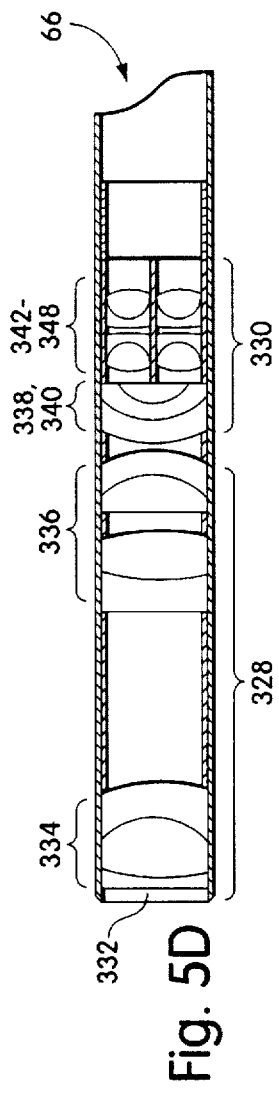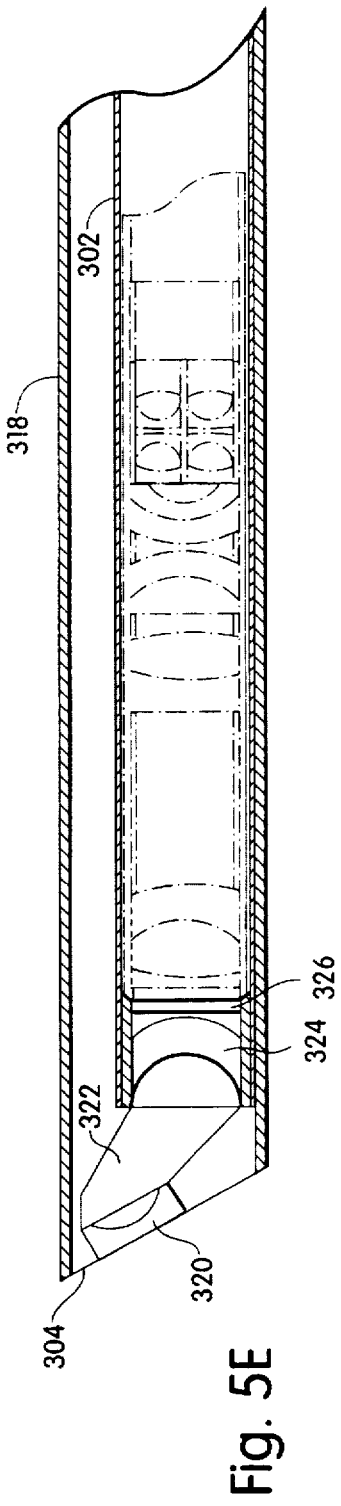

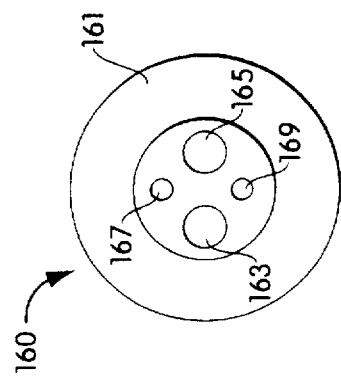
Fig. 9C
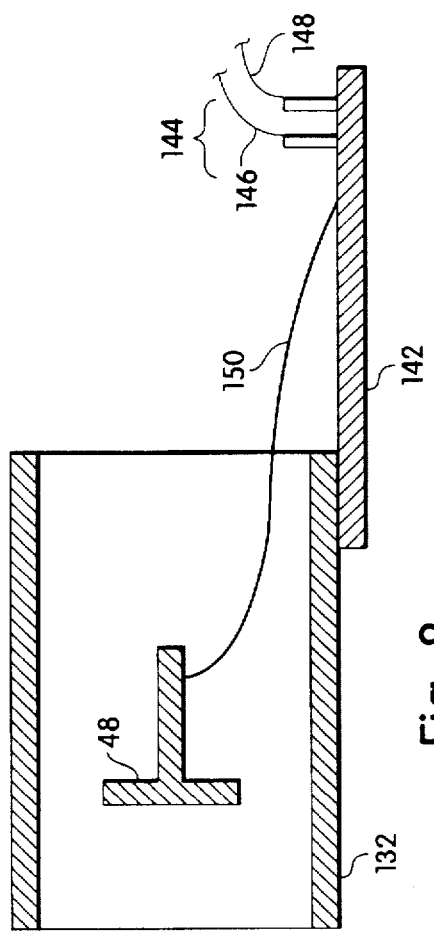
Fig. 8
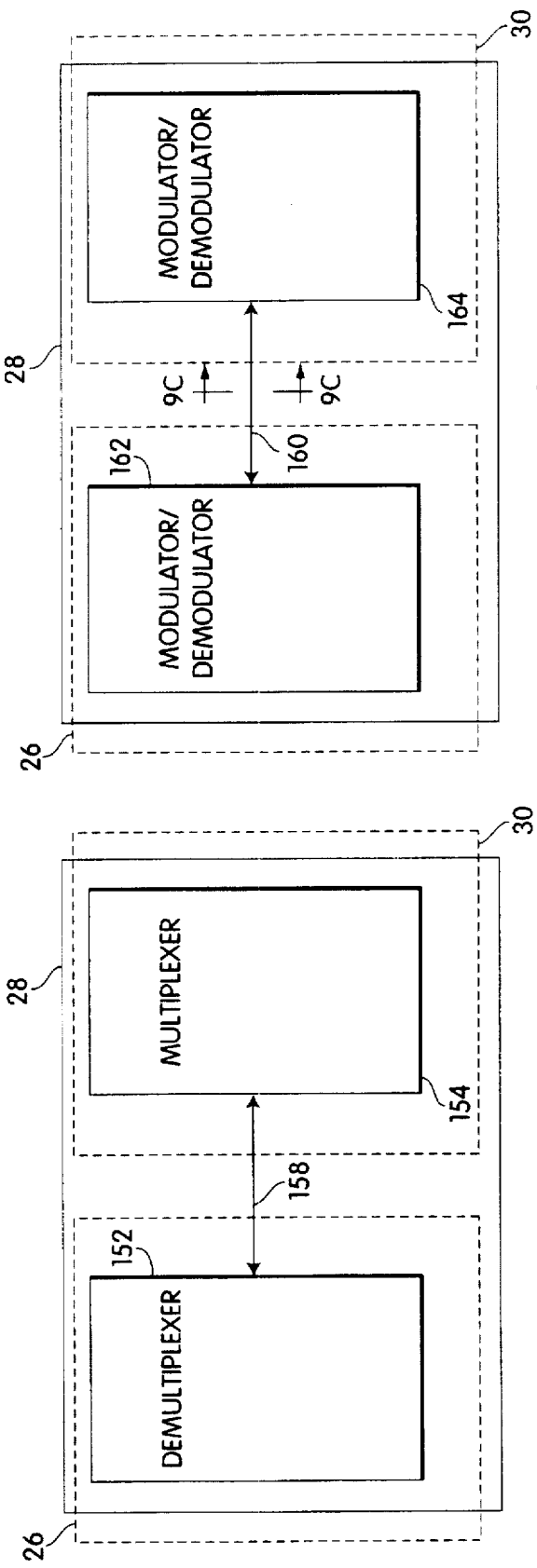
Fig. 9B
Fig. 9A

STEREOSCOPIC ENDOSCOPE SYSTEM

CROSS-REFERENCE TO RELATED APPLICATIONS

This is a continuation of U.S. application Ser. No. 08/227,675, filed Apr. 14, 1994 for "Medical Video Endoscope System" now abandoned, which is a continuation-in-part of U.S. patent application Ser. No. 08/000,664 which was filed on Jan. 5, 1993, now abandoned, and a continuation-in-part of U.S. patent application Ser. No. 08/076,544 which was filed on Jun. 14, 1993, now abandoned.

FIELD OF THE INVENTION

This invention relates to medical video endoscope systems used to examine the interior of a body cavity or a hollow organ, and more particularly, to a stereo video medical endoscope system.

BACKGROUND OF THE INVENTION

Medical video endoscope systems are used to visualize internal regions of patients during minimally-invasive diagnostic and surgical procedures. Such systems typically include a medical endoscope (such as an arthroscope, a laparoscope, or a colonoscope) which can be a rigid or flexible tubular optical instrument of various diameters and lengths for insertion through an opening, natural or surgical, in the body. The optical instrument typically is connected to a video camera. When the instrument is inserted and positioned for use within the patient's body, an image of the interior of the body is displayed, for example, on a monitor. The image displayed is two-dimensional.

In many instances, a user (e.g., a physician) desires visual images of the interior of the body that are more accurate and realistic than conventional two-dimensional images. A surgeon provided with only a conventional two-dimensional image of the patient does not perceive depth and thus the surgeon typically experiences a reduction in hand-eye coordination. For example, the surgeon typically experiences difficulty in accurately locating and positioning surgical instruments when provided with a conventional two-dimensional image. The surgeon also typically becomes fatigued quickly due to the intense concentration required to perform accurate surgical techniques with such a conventional image. Furthermore, it is typically difficult for the surgeon to quickly and accurately identify portions of the patient such as various tissues and organs with only a conventional two-dimensional image.

A medical video endoscope system capable of producing high-resolution, binocular, color, real-time, stereoscopic, three-dimensional images would provide the user with more accurate and realistic images.

SUMMARY OF THE INVENTION

A medical video endoscope system according to the invention provides an integrated system which meets or exceeds current industry standards for medical video endoscopes and produces high resolution images (e.g., on a monitor connected to the system) which a properly-equipped user/viewer of the system will perceive as three-dimensional images having stereoscopic depth. With this system, the viewer is provided with excellent visual perception because of stereopsis, the phenomenon of simultaneous vision with two eyes in which there is vivid perception of the distances of objects from the viewer. Stereopsis is present because the two eyes view objects in space from two points so that the retinal image patterns of the same object are slightly different in the two eyes.

In general, in one aspect, the invention features a high resolution medical video endoscope system which comprises: (A) a stereoscopic endoscope having a barrel portion and a handle portion; (B) an electronic processor module; (C) a transmission channel for coupling the stereoscopic endoscope to the electronic processor module; (D) a viewing system to allow a user to view three-dimensional video images; and (E) a rigid sheath assembly into which at least the barrel portion of the stereoscopic endoscope is insertable such that the rigid sheath assembly can be rotated about and with respect to the barrel portion. The rigid sheath assembly includes an angled distal tip having a face and optics for directing optical images from the direction in which the face of the angled distal tip is pointed to the stereoscopic endoscope when the barrel portion thereof is inserted into the rigid sheath assembly. Rotation of the rigid sheath assembly causes changes in the direction in which the face of the angled distal tip is pointed, thereby allowing stereoscopic endoscope viewing direction changes when the barrel portion is inserted into the rigid sheath assembly.

In general, in another aspect, the invention relates to a high resolution medical video endoscope system which comprises: (A) a camera head coupling and adapting system for coupling to a conventional endoscope, receiving a two-dimensional optical image from the conventional endoscope, and processing the two-dimensional optical image to create a left video image signal and a right video image signal, which left and right signals are substantially the same; (B) an electronic processor module for processing the left and right signals as if they were true separate left and right signals generated by a stereoscopic endoscope; (C) a transmission channel for coupling the camera head system to the electronic processor module; and (D) a viewing system to allow a user to view two-dimensional video images.

Other aspects, features, and advantages of the invention will become apparent from the following description and from the claims.

BRIEF DESCRIPTION OF THE DRAWINGS

FIGS. 5C–5F show the distal end of the sheath assembly of FIG. 5B in more detail both with and without the barrel of the endoscope inserted therein.

FIG. 8 is a side view in cross-section of an image sensor mounted in a support structure within a handle of the stereoscopic endoscope.

FIGS. 9A and 9B are block diagrams of two possible embodiments of a transmission channel according to the invention.

FIG. 9C is a view in cross-section of a cable shown in FIG. 9B, taken along line C—C of FIG. 9B.

DETAILED DESCRIPTION

A medical video endoscope system which displays images having a binocular depth cue known as stereopsis will provide a viewer with images having a realistic, three-dimensional quality. Stereopsis involves the presentation of a first image of an object to one eye of the viewer and a second image of the object to the other eye of the viewer where the two images are taken from different perspectives. Each eye of the viewer thus sees a slightly different perspective of the same object which the viewer's mind synthesizes into a three-dimensional image of the object having stereoscopic depth.

Figure 1:
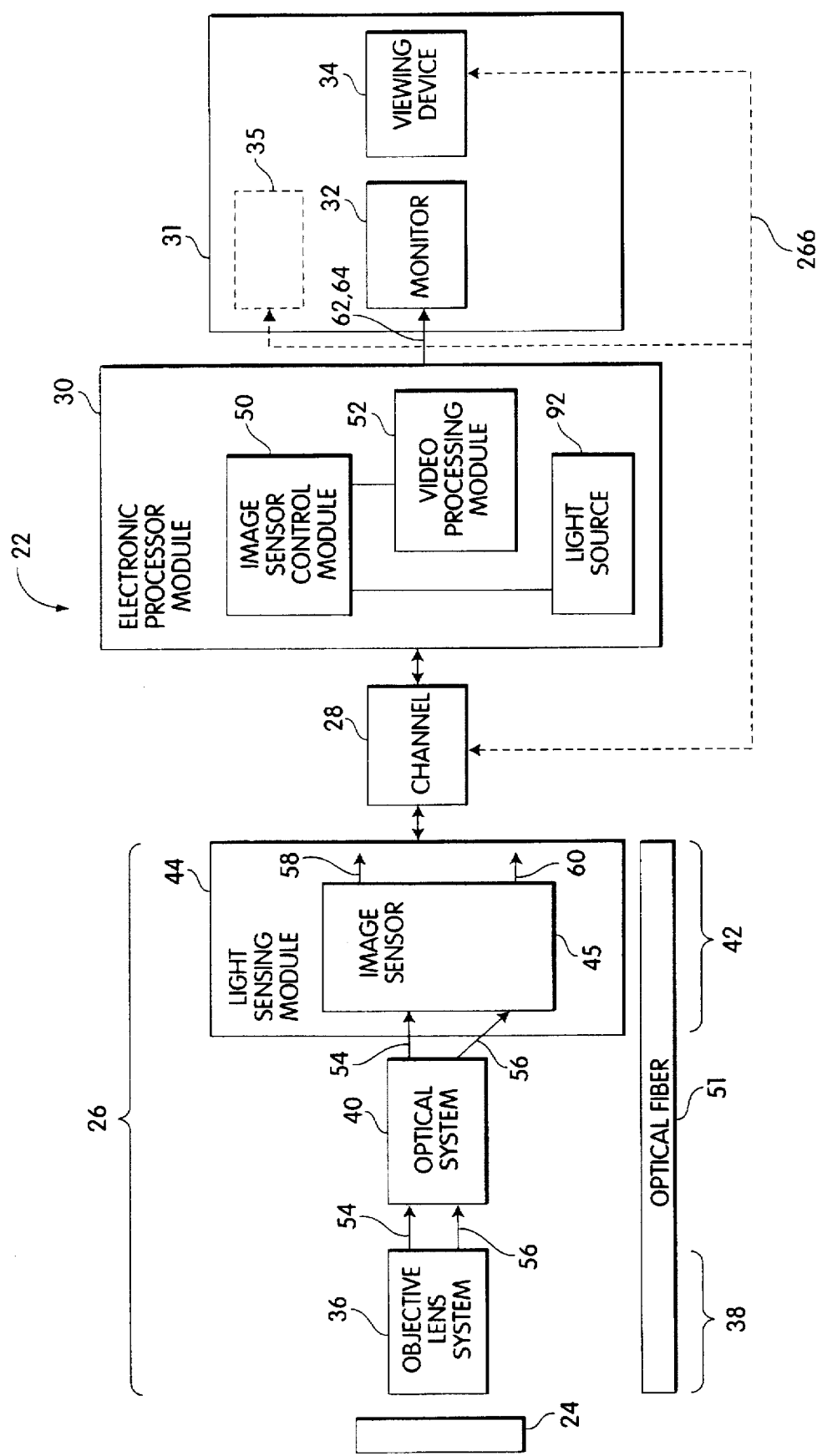
FIG. 1 is a block diagram of a medical video endoscope system according to the invention.

Referring to FIG. 1, according to the invention, a medical video endoscope system 22 for viewing high resolution three-dimensional images of an object 24 is shown. A stereoscopic endoscope 26 produces two optical images of the object 24, namely a first (e.g., left) optical image 54 and a second (e.g., right) optical image 56, and converts the two images into signals 58, 60. A transmission channel 28 generally receives and carries the signals 58, 60 from the stereoscopic endoscope 26 to an electronic processor module 30 which processes the signals 58, 60 to generate left image signals 62 and right image signals 64. Module 30 alternately provides the left and right image signals 62, 64 to a viewing system 31 which includes a monitor 32 and a viewing device 34 (e.g., specially-designed eyeglasses). The monitor 32 displays alternating left and right video images corresponding to the alternately-provided image signals 62, 64. A properly-equipped viewer of the monitor 32 will perceive three-dimensional video images of the object 24 due to the repeatedly alternating left and right video images displayed on the monitor 32.

(Note that, in general, it is irrelevant whether the left or the right video image is displayed "first", or, similarly, whether the left or the right image signal is provided to the monitor "first", because the alternation between left and right occurs repeatedly during operation of the system 22. Thus, any reference herein to "left and right" shall mean either "left and right" or "right and left.")

Instead of the monitor 32 and the viewing device 34, the viewing system 31 can include a video projector system 35 which receives the alternately-provided signals 62, 64 and, for example, projects corresponding polarized images onto a screen for viewing with polarized eyewear.

Figure 14:
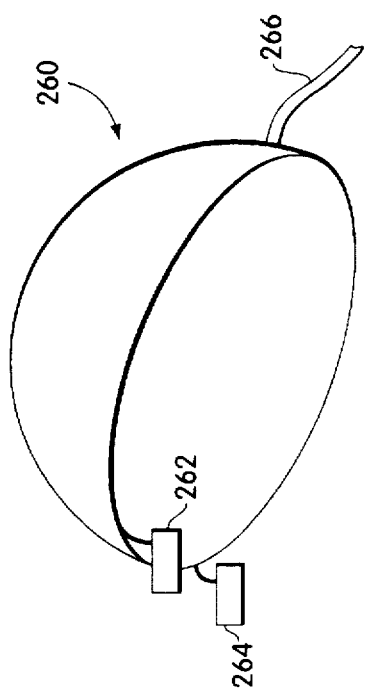
FIG. 14 is a diagram of another viewing device for use with the medical video endoscope system.

In other embodiments, the transmission channel 28 can couple the stereoscopic endoscope 26 either directly to the viewing device 34 which can be, for example, a headset as in FIG. 14 (thus bypassing the electronic processor module 30 and the monitor 32), or directly to the video projector system 35 which can include, for example, two video projectors for projecting, respectively, left and right polarized images onto a screen (thus bypassing the electronic processor module 30, the monitor 32, and the viewing device 34). In the latter embodiment, the polarized images can be viewed with polarized eyewear, and any type of screen can be used such as a flat screen.

In the high resolution medical video endoscope system 22 according to the invention, the stereoscopic endoscope 26 includes a stereoscopic objective lens system 36, disposed at a distal end 38 of the endoscope 26, for producing the left optical image 54 and the right optical image 56 of the object 24, and a relay lens system or an optical fiber system 40 disposed within the endoscope 26 and proximal to the objective lens system 36 for transmitting the left and right optical images 54, 56 along the length of the endoscope 26 towards a proximal end 42 of the endoscope 26. The stereoscopic endoscope 26 also includes a light sensing module 44 having an image sensor 45 disposed generally at the proximal end 42 of the endoscope 26. The sensor 45 senses (typically periodically) the left and right optical images 54, 56 for a period of time which can be adjusted (e.g., to compensate for ambient light variations and thus correct brightness variations in the video image displayed on the monitor 32) automatically (e.g., by the module 50) and converts these images 54, 56 to the signals 58, 60 for transmission through the transmission channel 28. The stereoscopic endoscope 26 also preferably includes an optical fiber 51 extending therethrough for transmitting light generated by a light source 92 to illuminate the object 24.

The electronic processor module 30 includes an image sensor control module 50 for controlling the image sensor 45 and for receiving the signals 58, 60 from the transmission channel 28. The electronic processor module 30 also has a video processing module 52 for receiving the signals 58, 60 from the image sensor control module 50, reformatting the signals 58, 60 into time-multiplexed left and right image signals 62, 64, and alternately providing the reformatted left and right image signals 62, 64 to the monitor 32 which displays alternating left and right video images corresponding to the signals 62, 64.

The viewing device 34 allows the viewer to observe high resolution stereoscopic video images of the object 24 on the monitor 32 by permitting a first eye of the viewer to see only the left video images displayed on the monitor and a second eye of the viewer to see only the right video images displayed on the monitor. The viewer thus perceives the alternating left and right video images displayed on the monitor as three-dimensional video images of the object 24 having stereoscopic depth.

Figure 2A:
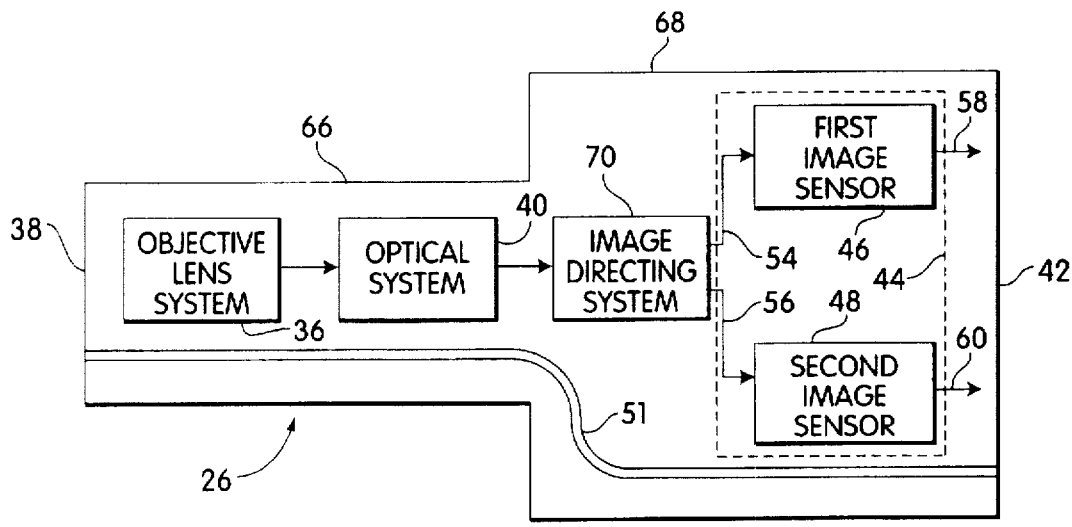
FIGS. 2A and 2B are each a block diagram of an embodiment of a stereoscopic endoscope which is a portion of the medical video endoscope system.
Figure 3:
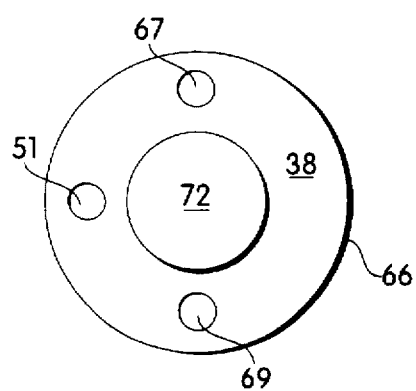
FIG. 3 is an end view of the stereoscopic endoscope.

Referring to FIGS. 2A and 3, in one embodiment of the medical video endoscope system according to the invention, the stereoscopic endoscope 26 has a barrel 66 and a handle 68. The barrel 66, which is tubular, houses the objective lens system 36, the relay lens or optical fiber system 40, and the optical fiber 51. The barrel 66 can be rigid or flexible. The handle 68 contains an image directing system 70 (described below), the light sensing module 44, and the optical fiber 51. The barrel 66 and the handle 68 each can be provided in a variety of sizes and shapes. For example, the barrel 66 can range from 10 cm to 70 cm in length and from 1 mm to 20 mm in diameter.

In one embodiment, the barrel 66 and the handle 68 can be separated to allow cleaning and sterilization of the barrel 66 while another barrel (which can have a different length and/or diameter) is attached to the handle 68 and the endoscope 26 (including the handle 68 and the replacement barrel) is used. The barrel 66 (or any replacement barrel), whether separable from the handle 68 or not, can include a passage 67 through which water can be passed to clean, for example, the lens system 36. The barrel 66 also can include a similar passage 69 through which a surgical tool can be passed thus minimizing the number of surgical punctures created in a patient's body.

In the disclosed embodiment, the image sensor 45 of the light sensing module 44 includes a first image sensor 46 and a second image sensor 48. The first image sensor 46 converts the left optical images 54 to the signals 58, and the second image sensor 48 converts the right optical images 56 to the signals 60.

Figure 2B:
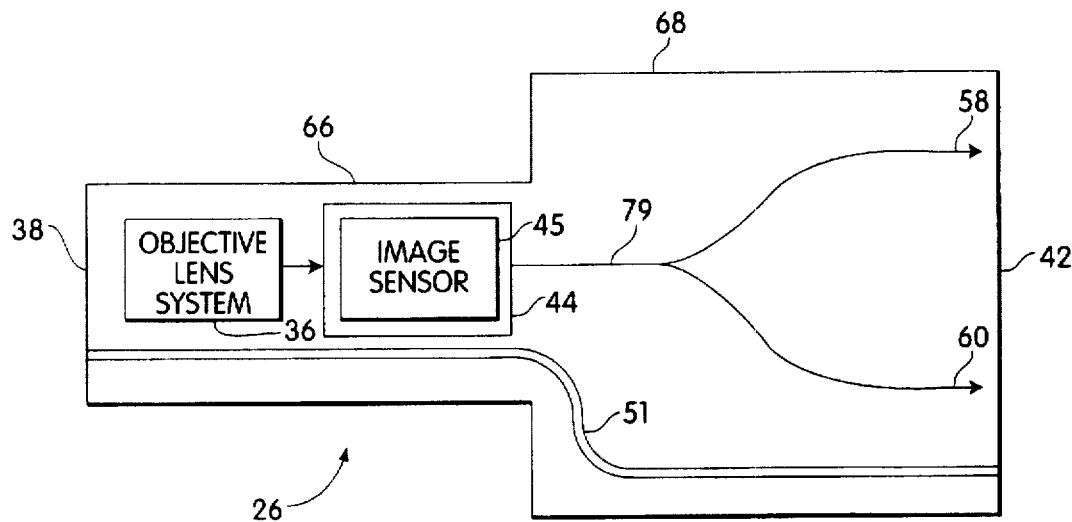

Referring to FIG. 2B, in another embodiment of the medical video endoscope system according to the invention, the barrel 66 houses the objective lens system 36, the light sensing module 44, and cables or wires 79 which extend from the module 44 through the barrel 66 and the handle 68 to the proximal end 42 of the endoscope 26. The wires 79 transmit the signals 58, 60 from the module 44 to the channel 28. The wires 79 can be conventional electrical signal-carrying conduits such as one or more copper wires. In this embodiment, the module 44 is mounted in close proximity to the objective lens system 36 thereby eliminating the need for the system 40 as well as the image directing system 70. The barrel 66 (or a portion thereof) can be made flexible because the wires 79 themselves typically are flexible. (Note that the barrel 66, the handle 68, and the light sensing module 44 can be as described above in relation to FIGS. 2A and 3.)

Figure 4A:
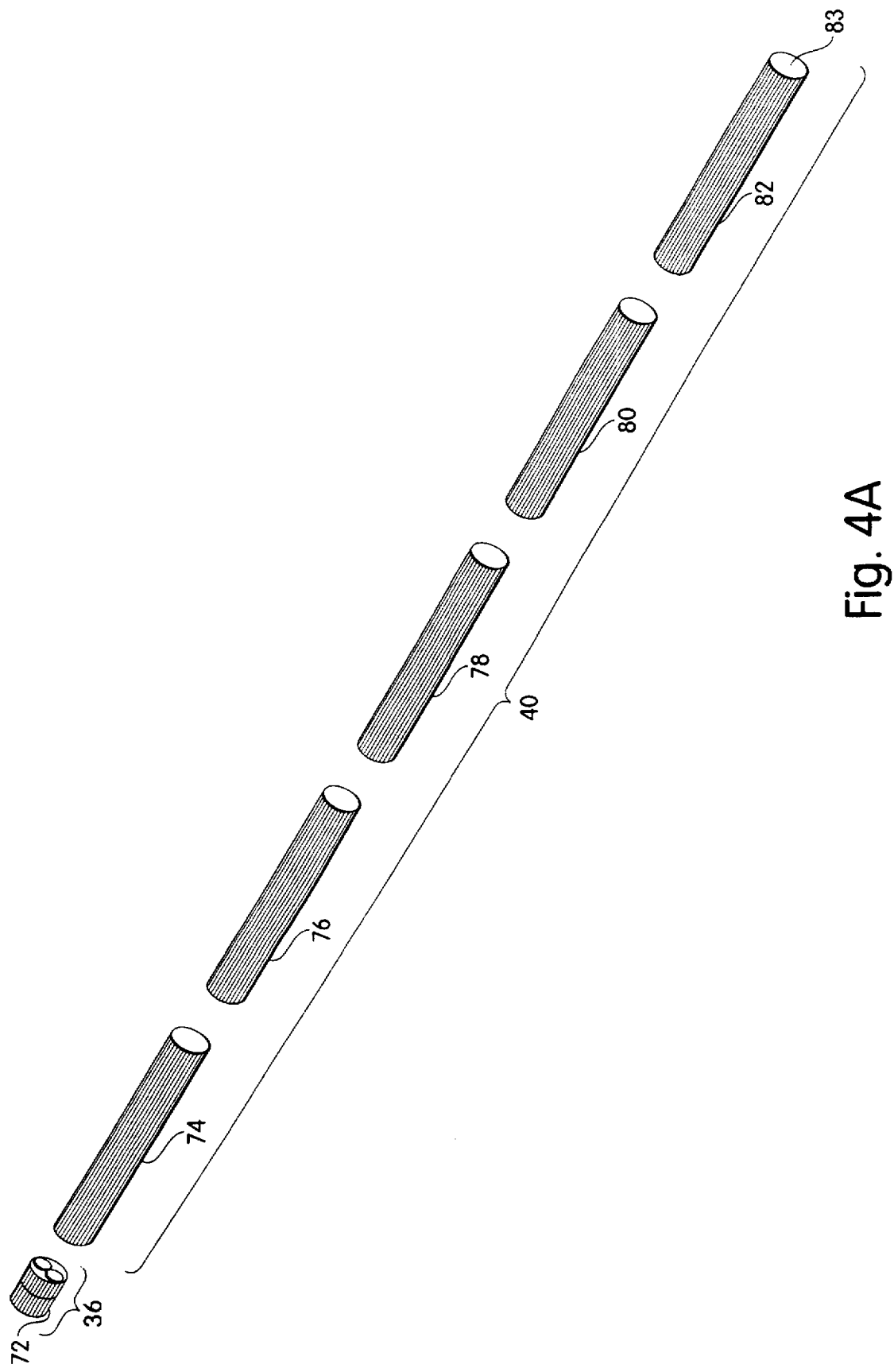
FIGS. 4A, 4B, and 4C are diagrams of optics housed within a barrel of the stereoscopic endoscope.
Figure 4B:
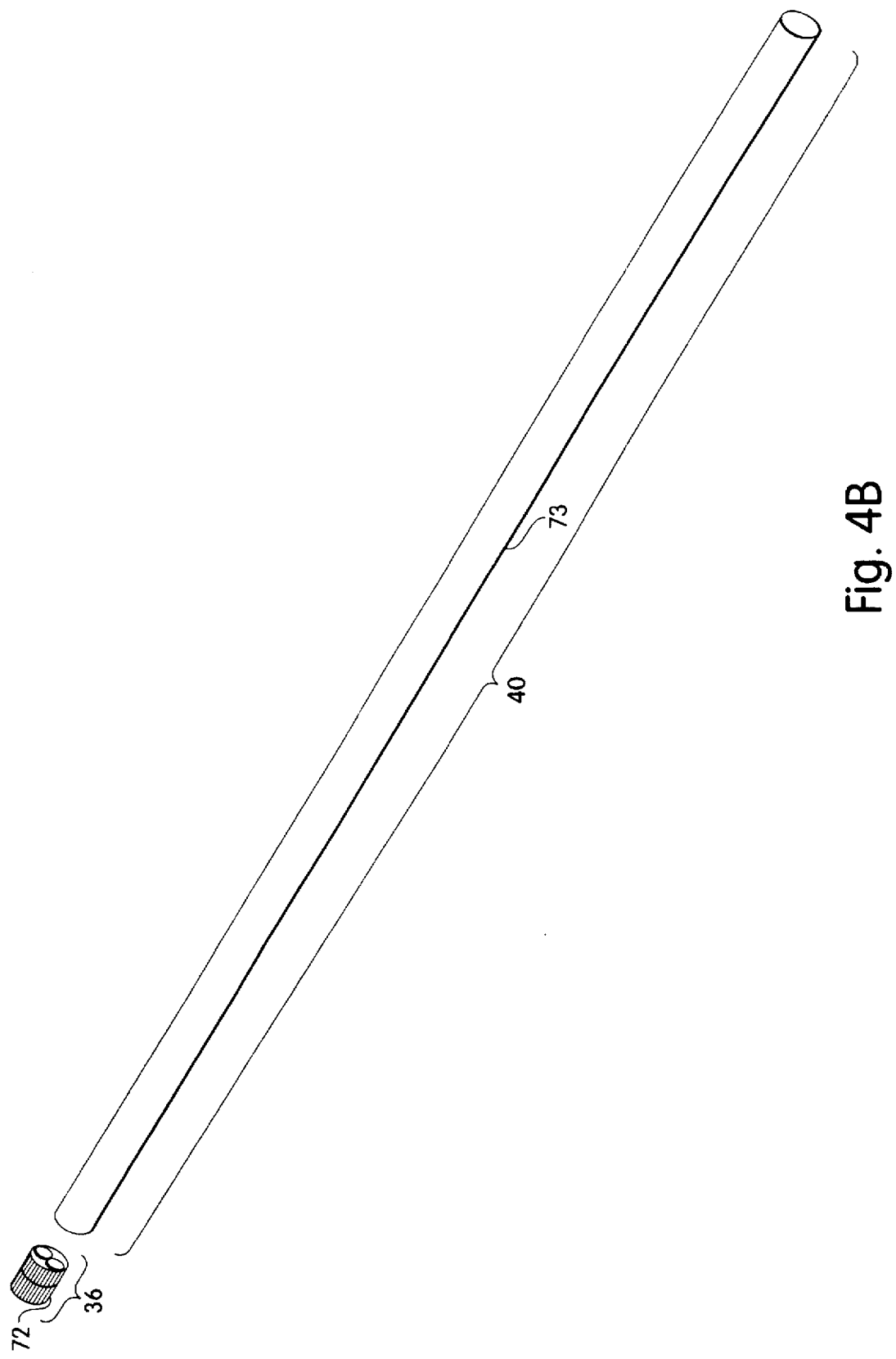
Figure 4C:
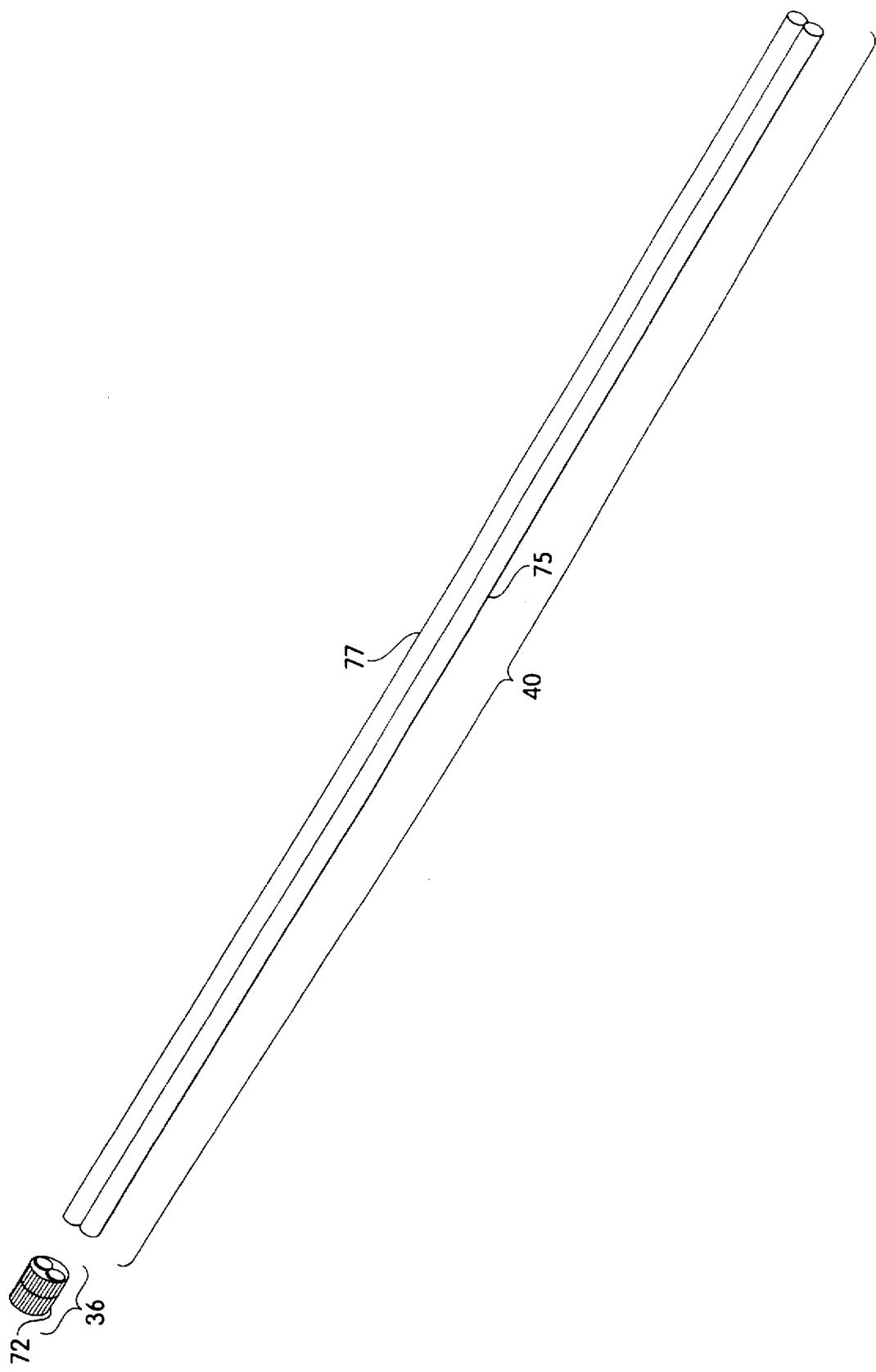

As shown in FIGS. 4A, 4B, and 4C, the objective lens system 36 can be a stereo cell 72. Referring to FIG. 4A, the system 40 can be a series of five separate relay lenses 74, 76, 78, 80, and 82. As will be appreciated by one of ordinary skill in the art, the relay lens system can include a different number of separate relay lenses. Also, instead of one or more relay lenses, the relay lens system 40 can be a gradient index lens system. An acceptable objective lens system 36 is described in U.S. Pat. No. 5,122,650 which issued on Jun. 16, 1992 to McKinley and U.S. Pat. No. 5,191,203 which issued on Mar. 2, 1993 to McKinley. An acceptable relay lens system 40 is described in U.S. Pat. Nos. 5,122,650 and 5,191,203, and also in U.S. Pat. No. 5,097,359 which issued on Mar. 17, 1992 to McKinley and U.S. Pat. No. 5,059,009 which issued on Oct. 22, 1991 to McKinley.

Referring to FIG. 4B, the system 40 can be a single optical fiber bundle 73 having a plurality of individual coherent optical fibers therein. In general, the optical fiber bundle includes at least one optical fiber for every pixel of the first image sensor 46 and the second image sensor 48. In one embodiment, the number of individual optical fibers is of the order of a few million (e.g., about three million fibers).

Sampling theory suggests that about 2.4 optical fibers should be used for each pixel to avoid degrading the image, but applicants believe two fibers per pixel provides a substantially non-degraded image and one fiber per pixel provides an image of acceptable quality.

Referring to FIG. 4C, the system 40 can be two optical fiber bundles 75, 77 which each have a plurality of individual coherent optical fibers therein. As described with relation to FIG. 4B, each bundle includes at least one optical fiber for every pixel of one of the sensors 46, 48. In one embodiment, the number of individual optical fibers per bundle is of the order of a few million (e.g., about one million two hundred thousand fibers per image sensor).

By using the optical fiber system 40 of either FIG. 4B or FIG. 4C, the barrel 66 (or a portion thereof) of the endoscope 26 can be made flexible because the fibers themselves typically are flexible.

Figure 5A:
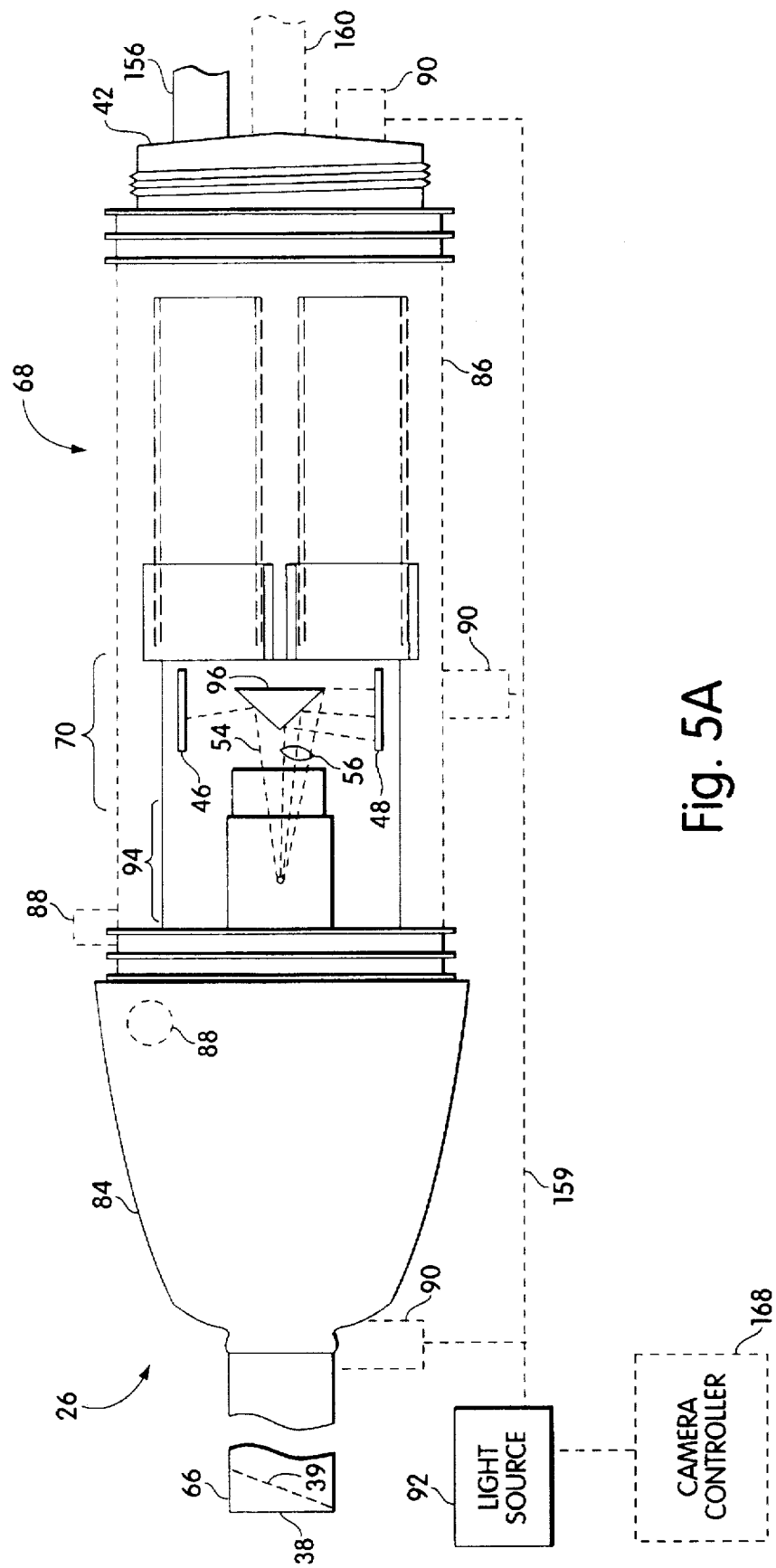
FIG. 5A is a diagram showing a handle of the stereoscopic endoscope in cut-away.

In one embodiment of the handle 68, as shown in FIG. 5A, the barrel 66 connects to a nose cone 84 which forms a distal portion of the handle 68. A middle portion of the handle 68 has a grasping area 86. A user typically will view different objects by grasping the area 86 and manipulating the entire endoscope 26 to point the distal end 38 of the endoscope 26 at an object to be viewed. To alleviate the need to manipulate the entire endoscope 26 in order to "look around", the objective lens system 36 at the distal end 38 of the endoscope 26 can be made movable, possibly via a mechanical actuating mechanism 88, such as a rotatable knob located on, for example, the nose cone 84 or the grasping area 86. Alternatively, the distal end 38 can be made flexible or formed at a fixed angle as indicated by a dotted line 39 in FIG. 5A.

Figure 5F:
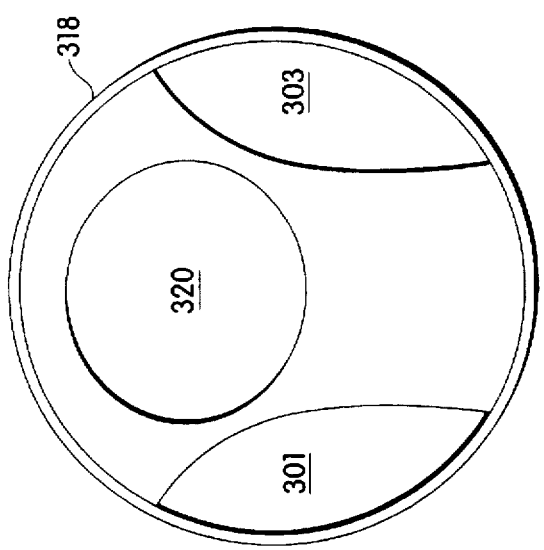
Figure 5B:
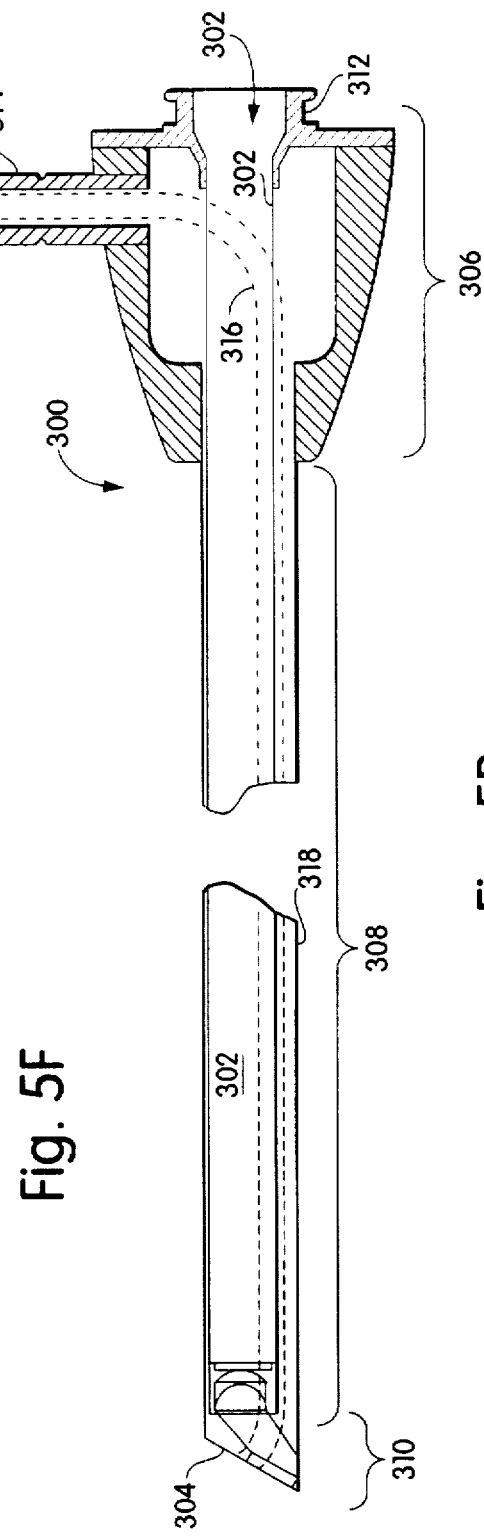
FIG. 5B is a drawing in cross-section of an angle-tipped sheath assembly which can be placed over the barrel of the stereoscopic endoscope and then rotated with respect to the barrel thereby changing the viewing direction of the endoscope.

Referring to FIG. 5B, an angle-tipped sheath assembly 300 can be provided to allow the endoscope viewing direction to be changed while the endoscope is being used. The sheath assembly 300 includes an inner tube 302 for receiving the barrel 66 of the endoscope 26. (The sheath assembly 300 is shown in FIG. 5B without the barrel 66 inserted in the inner tube 302.) Once the barrel 66 is inserted into the sheath assembly 300, the entire sheath assembly 300 can be rotated with respect to the barrel 66 (and the rest of the endoscope 26) to change the viewing direction of the endoscope 26. The viewing direction changes because the angled face 304 of the distal tip of the sheath assembly 300 rotates as the sheath assembly 300 is rotated about the barrel 66. This provides the user with the ability to rotate the sheath assembly to provide additional stereo views.

The sheath assembly 300 includes a nose cone extension portion 306, a working length portion 308, and an angled tip portion 310. The nose cone extension portion 306 includes a sheath latch fitting 312 which mechanically couples to the nose cone 84 (FIG. 5A) of the endoscope 26 and which allows rotation of the entire sheath assembly 300 with respect to the endoscope 26. The nose cone extension portion 306 of the sheath assembly 300 also includes a light guide adapter fitting 314 for receiving light from a light source (e.g., the light source 92 of FIG. 5A). As indicated by the dotted lines 316 extending through the fitting 314 to the angled face 304 at the distal tip of the sheath assembly 300, the light from the light source can be carried to the distal end of the sheath assembly 300 by one or more optical illumination fibers. The working length portion 308 of the sheath assembly 300 includes the inner tube 302 and an outer tube 318 through which the optical illumination fiber(s) 316 can extend. The working length portion 308 can be made to any of a variety of lengths including lengths from 10 cm to 70 cm. The angled tip portion 310 of the sheath assembly 300 includes optics (referred to hereinafter as "field telescope") which carry images from the angled face 304 to the distal tip of the barrel 66 of the endoscope 26 when it is inserted in the inner tube 302 of the sheath assembly 300. The details of the angled tip portion 310 are described later with reference to FIG. 5C. Various angles are possible for the angled tip portion 310 including zero, 30, 45, and 70 degrees, as well as other angles. The angle shown in FIGS. 5B–5F is 30 degrees.

Referring to FIG. 5C, the field telescope of the angled tip portion 310 of the sheath assembly 300 includes a front negative lens 320, a prism 322, a rear positive lens 324, and a window 326. The distal end of the barrel 66 of the endoscope 26 can be placed in close proximity to the window 326 when the barrel 66 is inserted into the inner tube 302 of the sheath assembly 300. It generally is not desirable to allow the distal end of the barrel actually to contact the window 326. In FIGS. 5D and 5E, the distal portion of the endoscope barrel is shown before insertion into the inner tube 302 of the sheath assembly 300 (FIG. 5D) and after insertion thereinto (FIG. 5E). In FIG. 5E, the distal end of the barrel is placed in close proximity to the window 326 of the field telescope in the sheath assembly 300. The barrel 66 includes a pupil relay 328 and a stereo objective 330. (Proximal to the pupil relay 328 and the stereo objective 330 is the optical system 40 which, as described elsewhere, can include a relays lens system or a fiber optic system.) The pupil relay 328 includes a window 332 (which is placed in close proximity to, but generally does not actually touch, the window 326), a first doublet 334, and a second doublet 336. The stereo objective 330 includes six doublets 338, 340, 342, 344, 346, and 348. In FIG. 5E, the barrel 66 which is inserted in the inner tube 302 is shown in dotted lines, and the optical illumination fiber bundle 316 is not shown for clarity. In FIG. 5F, an end view of the angled tip portion 310 (looking directly into the angled face 304) shows the outer tube 318, the front negative lens 320, and channels 301 and 303 for the optical illumination fiber(s).

In one embodiment, the sheath assembly 300 and endoscope barrel 66 shown in FIGS. 5B–5F have the following dimensions. The outer tube 318 has an outer diameter of about 12 mm. The inner tube 302 has an inner diameter of about 8 mm. The barrel 66 of the endoscope 26 has an outer diameter of about 8 mm. Other dimensions are possible. For example, the outer diameter of the endoscope barrel can be about 5 mm, and the sheath assembly diameters can be sized accordingly. In general, as stated previously, the diameter of the barrel can range from about 1 mm to about 20 mm. The sheath assembly 300 can be made from stainless steel. Other materials also can be used for the sheath assembly 300.

Referring back to FIG. 5A, the handle 68 can have a fitting 90 for receiving light from the light source 92 via a cable 159 (e.g., an optical fiber). The fitting 90 can be located, for example, between the barrel 66 and the nose cone 84, on the grasping area 86, or preferably at the proximal end 42 of the endoscope 26. Locating the fitting 90 at the proximal end 42 of the endoscope 26 allows a user to grasp the area 86 without interference from the cable 159. If the fitting 90 is located either between the barrel 66 and the nose 84 or on the grasping area 86, a user typically must hold the cable 159 with the same hand grasping the area 86 in order to keep the cable 159 from getting in the way. With the fitting 90 at the proximal end 42, a user does not need to expend effort to keep the cable 159 out of the way; the user can concentrate solely on performing an accurate medical procedure. The light typically travels from the light source 92 through the cable 159 which is connected to the fitting 90 and through the optical fiber 51 disposed within the endoscope 26 to illuminate the object 24 (FIG. 1). In a current embodiment, the light source 92 is a xenon bulb having a maximum output power of 300 Watts.

Still referring to FIG. 5A, the grasping area 86 of the handle 68 houses the image directing system 70, the first and second image sensors 46, 48 of the light sensing module 44, and possibly a portion 94 of the system 40 (whether a relay lens system as in FIG. 4A, or an optical fiber system as in FIG. 4B or FIG. 4C). The image directing system 70 directs the left and right optical images 54, 56 from the system 40 onto the first and second image sensors 46, 48. In the disclosed embodiment, the image directing system 70 includes a prism 96. If the sensors 46, 48 are located differently, the system 70 also can include folding mirrors to reflect the images coming from the prism 96 to the sensors 46, 48.

Figure 6:
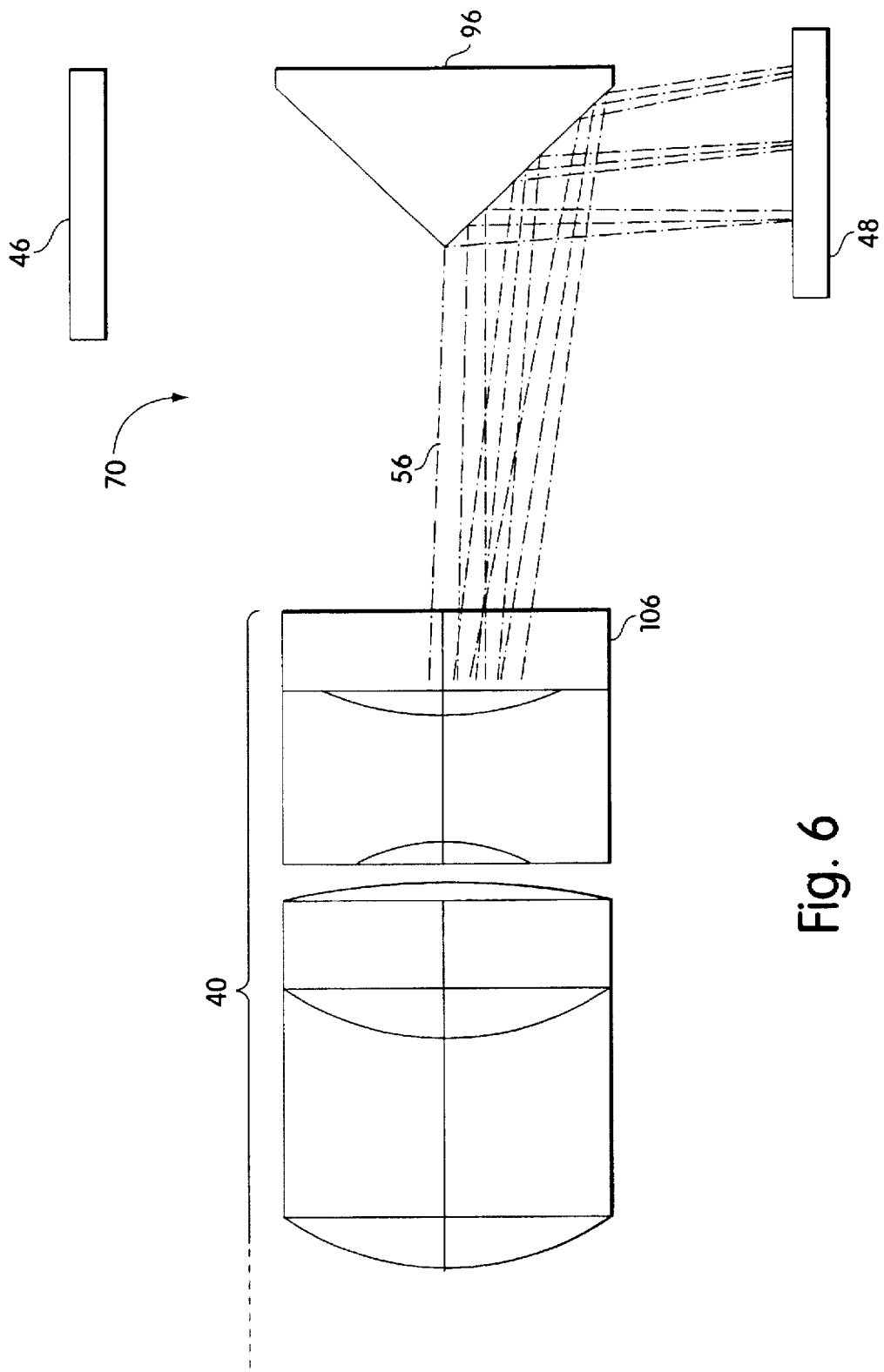
FIG. 6 is a diagram of an image directing system of the stereoscopic endoscope.

Referring to FIG. 6, each of the two optical images 54, 56 (only one is shown in FIG. 6 for simplicity) exiting the end of the system 40 is redirected by the prism 96 onto one of the two image sensors 46, 48. The first and second image sensors 46, 48 are located at a first and a second image focal plane, respectively.

If the system 40 is a relay lens system as in FIG. 4A, the system 40 can have a color filter 106 to compensate for certain characteristics of various components of the medical video endoscope system 22. For example, if the image sensors 46, 48 tend to produce images having a disproportionate amount of red color, the color filter 106 can be a blue/green filter which corrects the color response of the image sensors 46, 48.

The color filter 106 also can attenuate light of a particular wavelength before the light enters the image sensors 46, 48. For example, if laser light is introduced by a separate laser (not shown) and the image sensors 46, 48 are sensitive to the light laser (e.g., of 1064 nm) such that without attenuation of the laser light the image sensors 46, 48 do not produce meaningful signals, the color filter 106 can be used to attenuate the laser light by a factor of about one million.

As will be appreciated by one of ordinary skill in the art, other means of directing the images 54, 56 onto the image sensors 46, 48 besides the image directing system 70 are possible. Also, the image sensors 46, 48 can be located in different physical positions within the endoscope 26. Also, it is possible to eliminate the image directing system 70 entirely.

Figure 7:
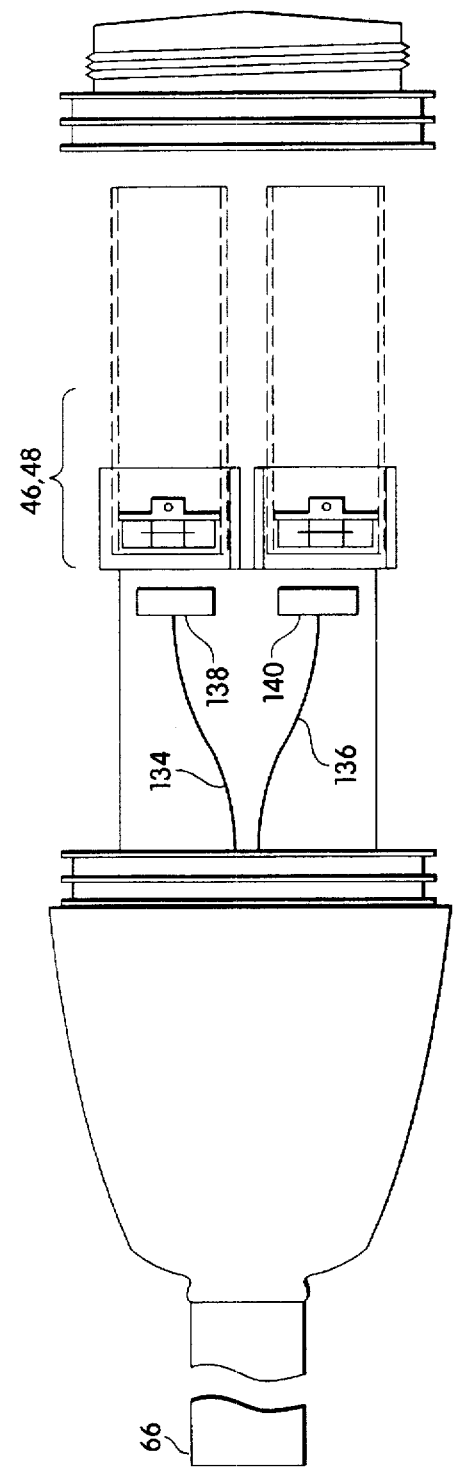
FIG. 7 is a cut-away diagram of a handle of a stereoscopic endoscope within which optical fibers are used to carry images to image sensors.

As shown in FIG. 7, the image directing system 70 is eliminated and optical fibers 134, 136 are used to carry the left and right optical images 54, 56 directly to the first and second image sensors 46, 48, which are now located as indicated. In this embodiment, lenses 138, 140 are placed at the ends of the fibers 134, 136 to focus the images on the image sensors 46, 48. While each of the fibers 134, 136 is shown as a single line, each can be a plurality of individual coherent optical fibers as described previously in relation to FIGS. 4B and 4C. The fibers 134, 136 can extend from a termination point 83 (FIG. 4A) of the relay lens system 40, or the fibers 134, 136 can be the plurality of fibers which run through the barrel 66 of the endoscope 26 to the objective lens system 36 as in FIG. 4B or 4C.

In one embodiment of a mechanical support structure within the handle 68, a nose cone mounts to a chassis, and the chassis has a central opening to allow passage of the left and right optical images 54, 56. The images are then incident upon the prism 96 of the image directing system 70. An assembly of the image directing system 70, which can be a metal (or other rigid material) block holding the prism 96, can be placed, for example, within a space formed in the chassis. It is useful to have the capability to make a multitude of adjustments because of the optical components used in the system 22. Adjustments typically will be made such that the left and right optical images 54, 56 are incident upon the centers of the first and second image sensors 46, 48. By adjusting the various components, the magnification and the optical image plane can be precisely set. In the disclosed embodiment, it is intended that all adjustments be performed during assembly (i.e., at the factory) and not by a user. Alternatively, the system can be designed to allow a user to make one or more adjustments. In any case, adjustments preferably allow correction of the optical image plane or back focal length to a fraction of one one-thousandth of an inch as measured along the optical axis. In one embodiment, focus is achieved by mechanical means operable, for example, by a user.

It also is possible to make various adjustments electronically. For example, horizontal and vertical alignment of images displayed on the monitor 32 can be performed by the electronic processor module 30.

Referring to FIG. 8, the second image sensor 48 can be mounted within an image sensor-holding sleeve 132, and a circuit 142 can be mounted to the sleeve 132. The circuit 142 can receive the output signals 60 of the image sensor 48 via one or more wires 150 and can have connectors 144 for providing the output signals 60. One or more wires 146, 148 can be connected to the connectors 144 to carry the output signals 60 of the image sensor 48 from the circuit 142. The first image sensor 46 can be mounted similarly.

Each of the first and second image sensors 46, 48 can be a charge-coupled device (CCD) camera. Suitable CCD cameras having 768 usable horizontal pixels are commercially-available. A commercially-available 1024 by 512 pixel CCD camera can be used, in which case the image directing system 70 would not be needed. One type of suitable CCD cameras are known as complementary color interline transfer cameras, which are the type currently used in "camcorders".

In another embodiment, less expensive black-and-white cameras can be used by employing a technique known as "sequential coloring". Sequential coloring is a technique in which different colors are sequentially sent from the light source 92 (FIG. 5A) under control of the electronic processor module 30. Thus, to employ the technique of sequential coloring, the light source 92 must be capable of generating different colors of light. Other types of cameras known to those of ordinary skill in the art also can be used.

In the embodiment shown in FIG. 5A, the transmission channel 28 which carries the signals 58, 60 output by the first and second image sensors 46, 48 is a camera cable 156 having coaxial cables and individual wires. Such a cable is known to those of ordinary skill in the art, and typically extends from the proximal end 42 of the endoscope 26. The light from the light source 92 typically is provided to the fitting 90 via the separate cable 159.

Referring to FIG. 9A, the number of wires or "lines" required for the transmission channel 28 can be significantly reduced by employing a demultiplexer 152 (associated with the image sensors 46, 48) and a multiplexer 154 (associated with the electronic processor module 30) in the transmission of signals between the stereoscopic endoscope 26 and the electronic processor module 30. A cable 158 connects the multiplexer 154 and the demultiplexer 152. When the embodiment of FIG. 9A is used, the light from the light source 92 (FIG. 5A) is provided to the fitting 90 on the handle 68 of the endoscope 26 via the cable 159 which is separate from the cable 158. Note that the demultiplexer 152 can be located within the stereoscopic endoscope 26 (preferably, within the handle 68 of the endoscope 26), and the multiplexer 154 can be located within the electronic processor module 30, as indicated by the dotted-line boxes in FIG. 9A.

Another embodiment of the transmission channel 28 is shown in FIGS. 9B and 9C. In this embodiment, a first modulator/demodulator (modem) 162 (associated with the image sensors 46, 48), a second modem 164 (associated with the electronic processor module 30), and a cable 160 are employed in the transmission of signals between the stereoscopic endoscope 26 and the electronic processor module 30. The cable 160 includes (i) an optical fiber 161 for carrying the light from the light source 92, (ii) two fiber optic bundles 163, 165, and (iii) two "solid" wires 167, 169. Referring to FIG. 5A, because one cable (cable 160) can carry all of the signals, the need for the fitting 90, the cable 159, and the cable 156 is eliminated, and the design of the endoscope 26 is simplified (i.e., only the cable 160 extends from the proximal end 42 of the endoscope 26). Referring back to FIG. 9B, note that the first modem 162 can be located within the stereoscopic endoscope 26 (preferably, within the handle 68 of the endoscope 26), and the second modem 164 can be located within the electronic processor module 30, as indicated by the dotted-line boxes.

In the embodiment of FIG. 9B, the modems 162, 164 can implement spread-spectrum communication techniques. Briefly and in general, in spread-spectrum techniques, the transmission bandwidth employed is much greater than the minimum bandwidth required to transmit the information. Spread-spectrum techniques can realize higher signal-to-noise ratios than other communication techniques. Other communication techniques also are possible.

Figure 10:
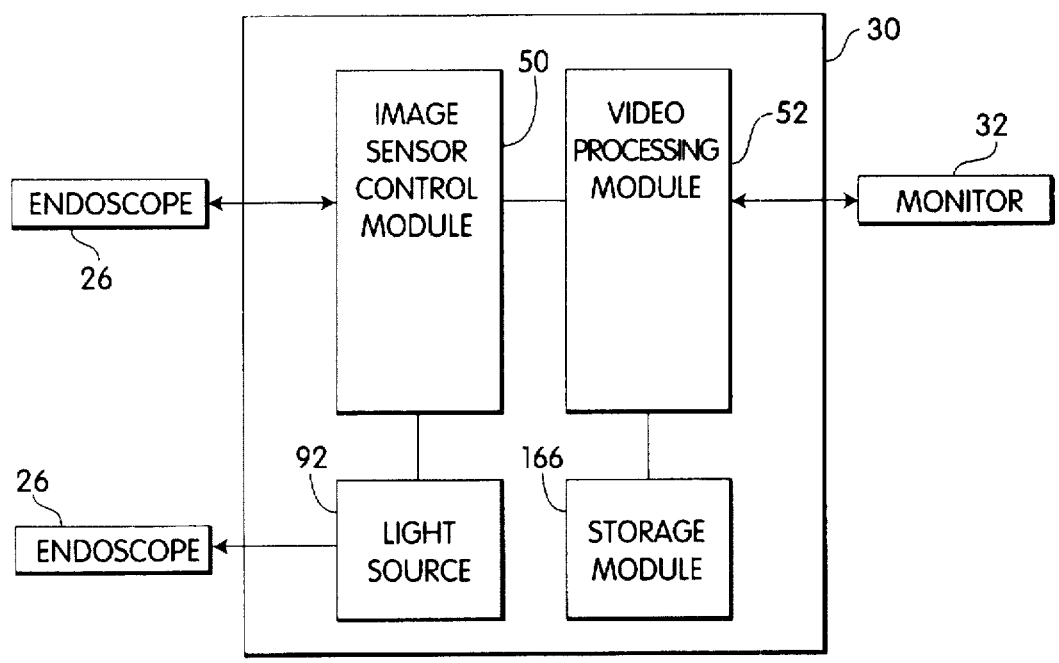
FIG. 10 is a block diagram of an electronic processor module of the medical video endoscope system.

Referring to FIG. 10, in the disclosed embodiment, the electronic processor module 30 includes the image sensor control module 50, the video processing module 52, and a storage module 166. The electronic processor module 30 provides all timing signals and video data paths between the image sensors 46, 48 in the endoscope 26 and the monitor 32. The electronic processor module 30 also can provide features which minimize a user's workload such as an auto exposure feature which automatically adjusts to varying light levels. White color balance can be provided as a user-adjustable feature. In one embodiment, the electronic processor module 30 is contained within two enclosures 214, 216 (see FIG. 11) and is powered in part by a UL/CSA-registered 300 watt power supply; the video processing module 52 can be powered by the 300 Watt power supply and the image sensor control module 50 can be powered by its own separate power supply.

Still referring to FIG. 10, the image sensor control module 50 can provide signals for the timing and control of each of the image sensors 46, 48 in the endoscope 26. The module 50 can accept complementary color interline transfer signals from each of the image sensors 46, 48 and convert these signals to national television standards committee (NTSC) format and/or to super video helical scan (S-VHS) format for processing and video tape recording. One skilled in the art will appreciate that a variety of other formats besides NTSC and S-VHS are possible. The module 50 also can provide additional integration control and color balance control for each of the image sensors 46, 48.

The image sensor control module 50 instructs the sensors 46, 48 to periodically sense the incident light (i.e., optical images) for a certain period of time in order to capture images of the object 24. The module 50 can automatically and dynamically adjust the brightness of the resulting video image in response to, for example, changing ambient light conditions by adjusting the amount of time the sensors 46, 48 sense the light incident upon them. The module 50 thus performs an electrical shuttering function to control the amount of light received by the sensors 46, 48 and correct for variations in brightness of the video image due to, for example, changing ambient light levels. This electrical shutter can adjust the brightness of the video image over a relatively limited dynamic range of ambient light, but it can correct for variations in the brightness of the video image very quickly. The image sensor control module 50 can be based on a commercially-available unit.

The video processing module 52 can accept the NTSC format (or the S-VHS format) signals from the image sensor control module 50 and reformat these signals to time-multiplexed red-green-blue (RGB) signals. The module 52 can store temporarily the signals from module 50 in a buffer while sending the reformatted signals to the monitor 32 at, for example, twice the input rate. The module 52 can generate signals to control, e.g., a liquid crystal modulator (described below) which changes the polarization characteristics of light emitted from the monitor 32. The video processing module 52 also can perform additional signal processing functions on the video signals such as color balance between video signals, intensity balance between video signals, adjustment of binocular disparity for comfort of the viewer, and graphics overlay signals providing borders and visual cueing. For example, a virtual image of a ruler or scale can be superimposed on images seen by a viewer of the monitor 32. The viewer will perceive the ruler to be in a plane in space in front of the endoscope, and the viewer can move the endoscope to place the image of the ruler in the apparent plane of an object to be measured.

Additionally, the video processing module 52 can perform signal processing functions on the video signals such as electronic zoom, hue adjustment, contrast adjustment, brightness adjustment, digital windowing techniques, metrology, and histogram averaging.

In one embodiment, the video processing module 52 is composed of commercially-available signal processing boards, custom-designed interfaces to provide signal switching, and software to setup proper operation of the circuitry and provide a diagnostic capability. Features of the module 52 can include: (i) two inputs, each input being a 0.7 Volt NTSC-encoded video signal, or a S-VHS-encoded video signal, at a rate of about 60 video frames per second and 525 horizontal video lines per frame, (iii) a Video Graphics Adapter (VGA) graphics overlay, (iv) a 0.7 Volt RGB video time-multiplexed output signal at a rate, to each eye, of about 60 video frames per second and at least 480 horizontal video lines per frame, non-interlaced, and (v) a 60 Hertz sync signal which can be supplied to, e.g., an infrared (IR) emitter or a liquid crystal modulator (described below).

The storage module 166 can provide program and data storage for operation of the image sensor control module 50 and the video processing module 52. The module 166 also can provide local and remote interfaces for diagnostic purposes.

In one embodiment, the storage module 166 is composed of a commercially-available processor, memory, floppy disk storage device for updating programs and data, and hard disk storage device for storing programs and data, all in an independent systems architecture (ISA) form factor. In another embodiment, the storage module 166 includes the processor, a read-only memory (ROM), and the floppy disk storage device but not the hard disk storage device. Another configuration includes only the processor and the ROM, and software is changed by burning it into another ROM and replacing the existing ROM.

Figure 11:
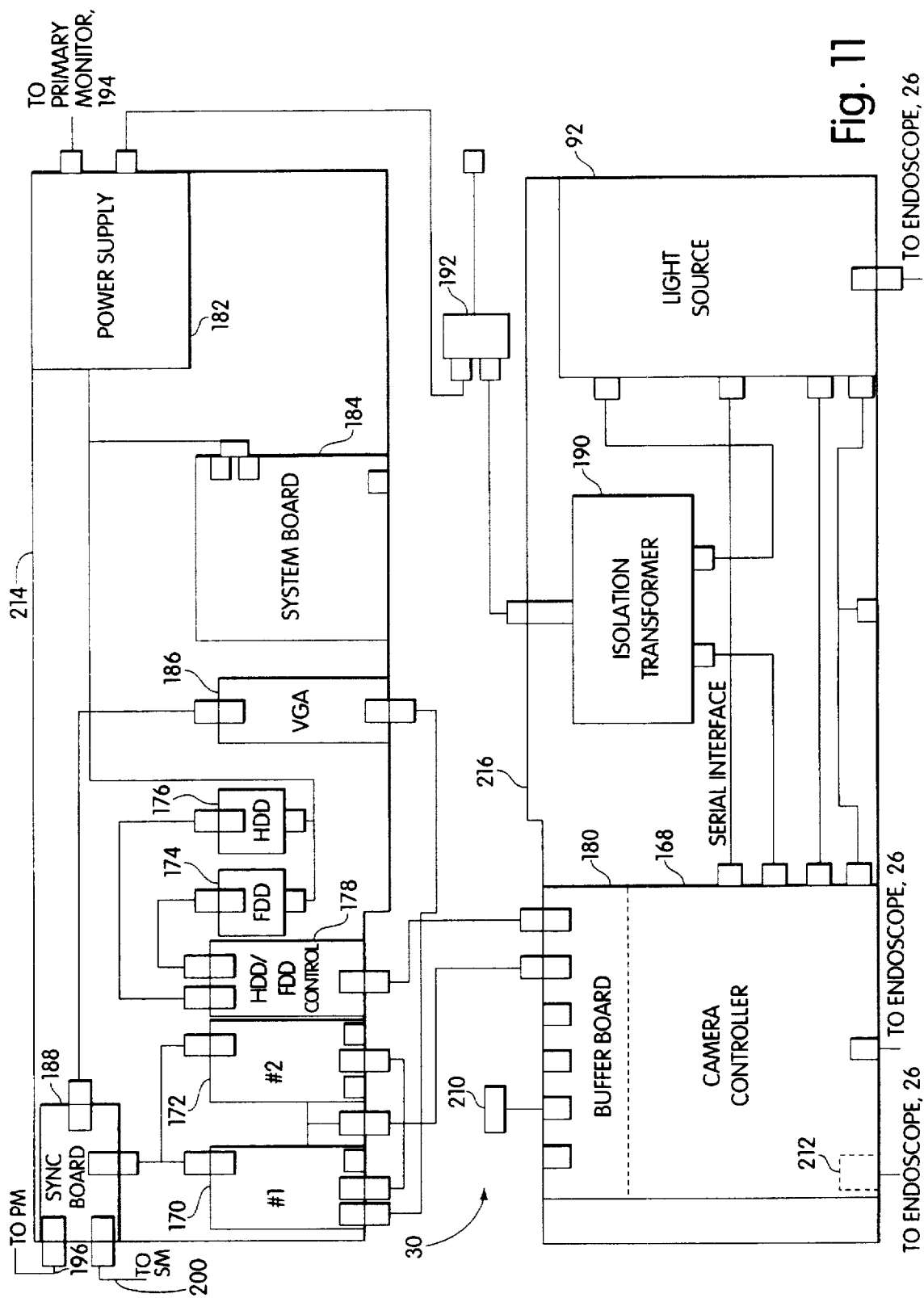
FIG. 11 is another block diagram of the electronic processor module.

Referring to FIG. 11, in the disclosed embodiment, two separate enclosures 214, 216 house components of the system. In FIG. 11, a camera controller 168, two motion video boards (or other image manipulation boards such as frame grabbers) 170, 172 (labeled #1 and #2), and the combination of a floppy drive 174, a hard drive 176, and a disk drive controller 178 (labeled FDD, HDD, and HDD/FDD CONTROL) represent, respectively and in general, the image sensor control module 50, the video processing module 52, and the storage module 166 of FIG. 10. A buffer board 180 for buffering and enhancing/driving signals is associated with the camera controller 168. Other components of the embodiment of FIG. 11 include the light source 92, a power supply 182, a system board 184, a VGA board 186, a sync board 188, an isolation transformer 190, and a power strip 192 which can be uninterruptable.

In general, the camera controller 168, the buffer board 180, and each of the two motion video boards 170, 172 can be based on commercially-available units. The system board 184 can include an Intel 80386 microprocessor or virtually any other general-purpose microprocessor.

The sync board 188, the motion video boards 170, 172, the floppy drive 174, the hard drive 176, the disk drive controller 178, the VGA board 186, the system board 184, and the power supply 192 (which can be uninterruptable), for example, can all be "cards" within the enclosure 214 which can be a personal computer housing.

In the disclosed embodiment, the VGA board 186, the sync board 188, and the two motion video boards 170, 172 cooperate to manipulate the signals from the endoscope 26 to generate stereoscopic video images.

The VGA board 186 generates the fundamental electronic signals of RGB video and delivers them to the sync board 188 via, for example, a feature connector of the sync board 188. The fundamental electronic signals include a vertical sync pulse, a horizontal sync pulse, a C blanking signal, a pixel clock signal, and color bits 0 through 7.

The sync board 188 buffers the majority of the signals received from the VGA board 186 and then passes them on to the two motion video boards 170, 172. The sync board 188 includes a flip flop which is clocked by the vertical sync pulse. The Q and Q-bar outputs of the flip flop, which are in a toggled state, are used to drive a vertical sync input of each of the motion video boards 170, 172. Because the Q and Q-bar outputs of the flip flop are 180 degrees out of phase, sequential video (described below) is possible. The sync board 188 also provides a frame sync pulse which switches a polarization bezel installed on the front of a monitor (described below).

One of the two motion video boards 170, 172 receives and translates information from one of the image sensors 46, 48 and the other motion video board receives and translates information from the other sensor. The camera controller 168 feeds NTSC (or S-VHS) encoded video information to the motion video boards 170, 172 which receive the information, translate it into a digital format, and store it in a frame buffer. This information is then read out of the frame buffer and fed to a video monitor via the sync board 188 in accordance with control signals provided to the boards 170, 172 by the sync board 188. This information is not necessarily read in and written out of the frame buffer at the same rate.

Signals output by the motion video boards 170, 172 are then passed back into the sync board 188 and united with signals generated by the sync board 188. All of these signals are then fed to the monitor(s) using, for example, C2 or C3 video cables.

Each of the motion video boards 170, 172 operate at a rate of at least 55 video frames per second, and preferably 60 video frames per second, which ultimately results in "flickerless" images (as perceived by a viewer) being displayed on the monitor 32. The two motion video boards 170, 172 can be replaced by a single board which allows complete pixel manipulation (i.e., "address resequencing").

A frame (or video frame) produced by the system described herein includes at least 480 horizontal lines wherein each line is unique; none of the lines of a frame are duplicated (by, for example, a "line doubler") to achieve the full 480 line frame. Any commonality between the lines of a frame is due to the optical characteristics of the object being viewed and not to any additional processing performed by the system to "pad" the frame with non-unique lines. A field contains less lines than a frame, typically half the number of lines as the frame or less. For example, a field typically contains only odd lines or only even lines such that every other line is missing. If a first field contains only the odd video lines of a complete frame and a second field contains only the even video lines of the frame, the two fields must be "combined" to create the complete frame.

The sync board 188 generates synchronization (i.e., timing) signals which indicate to the motion video boards 170, 172 when to release a frame. The motion video boards alternately release "left image" and "right image" frames, which each have at least 480 lines, to the connected viewing system 31 at a rate which is, for example, twice the rate of operation of each of the motion video boards 170, 172. For example, the board 170 releases a "left image" frame, the board 172 releases a "right image" frame, the board 170 releases another "left image" frame, the board 172 releases another "right image" frame, etc. That is, left images from one of the boards (e.g., board 170) are presented sequentially with right images from the other board (e.g., board 172) and presented to each eye of the viewer at a normal television rate (e.g., at least about 55 Hertz and preferably about 60 Hertz) such that each eye does not perceive any flicker.

Figure 16:
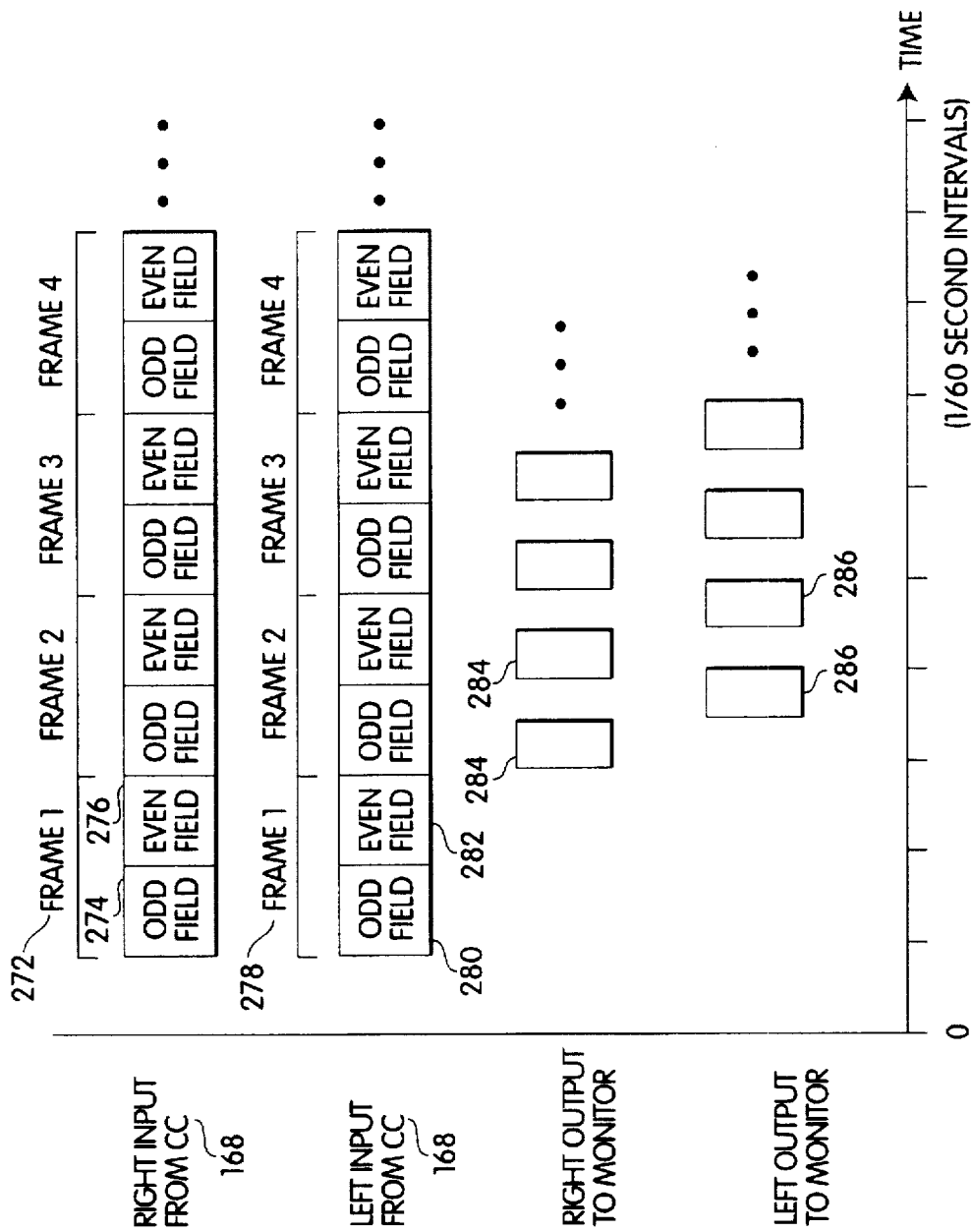
FIG. 16 is a timing diagram indicating the operation of motion video boards of the medical video endoscope system.

Referring to FIG. 16, a timing diagram indicates the manner in which the motion video boards 170, 172 receive NTSC (or S-VHS) encoded video information from the camera controller 168 and subsequently output the information to the monitor(s). In the disclosed embodiment, the intervals on the time axis are 1/60 seconds, but other rates which result in each eye of the viewer perceiving flickerless images on the monitor(s) also can be used such as intervals of 1/55 seconds.

As indicated in the timing diagram of FIG. 16, as one of the motion video boards (e.g., board 172) is receiving a first right frame 272 (which includes an odd field 274 and an even field 276) from the camera controller 168 (identified as CC), the other motion video board (e.g., board 170) simultaneously receives a first left frame 278 (which also includes an odd field 280 and an even field 282). Subsequent right and left frames (labeled FRAME 2, FRAME 3, and FRAME 4) are similarly simultaneously received from the camera controller 168 by each of the motion video boards 170, 172. In the disclosed embodiment, each motion video board receives a new complete frame every 1/30 seconds.

After being buffered in the frame buffer of the motion video board 172, the motion video board 172 releases a frame 284 having at least 480 lines and corresponding to the frame 272. The other motion video board 170 then releases a frame 286 which has at least 480 lines and corresponds to the frame 278. The board 172 then releases the frame 284 again, followed by another release of the frame 286 by the board 170. Thus, the boards 170, 172 sequentially release frames at a rate which is greater than the rate at which the frames are received. In the disclosed embodiment, the motion video boards 170, 172 together sequentially release frames every 1/120 seconds such that each eye of a viewer sees a complete, high-resolution frame every 1/60 seconds.

As the frames 284, 286 are being released, the motion video boards 170, 172 are concurrently receiving the next right and left frames (FRAME 2) simultaneously. The process thus continues in time such that each eye of the viewer sees a flickerless, complete, high-resolution video image frame.

In the disclosed embodiment, the sequentially-presented frames from the two motion video boards 170, 172 pass through the sync board 188 to a primary monitor 194 via a line 196 and to a secondary monitor 198 via a line 200. In general, the rate at which the frames are passed to each monitor is twice the rate of operation of each of the boards 170, 172 because of the sequential presentation that is performed. The sync board 188 also can generate timing signals for coordinating eyewear which allows a viewer to see three-dimensional images which have stereoscopic depth such as timing signals which tell a polarizing modulator associated with the monitor(s) when to alter its polarization (described below).

Note that each of the sequentially-presented image frames fully fills the screen of the monitor on which the image frame is displayed. That is, while the left and right image frames are presented sequentially, each image frame is not displayed on, for example, only half (or less) of the available lines of the monitor's screen such as just the odd video lines or just the even video lines. Instead, substantially all lines of the screen are used to display each image frame. Preferably, each frame contains at least 480 unique horizontal video lines. There is no "line doubling" performed; each image frame contains the complete and full number of video lines (e.g., all odd and all even video lines) which can possibly be displayed in the available bandwidth. Thus, the sequential presentation of left and right image frames is different from the interlacing of fields used with conventional television.

In general, each sequentially-presented image frame can contain multiple (e.g., 30) image data. That is, each such frame can include images from more than one data source. Possible data sources include the endoscope 26 (for real-time data), stored data, and data from another endoscope. Multiple images can be displayed on the monitor(s) simultaneously, for example, in a split screen (e.g., windowing) format.

The VGA board 186, the sync board 188, and the motion video boards 170, 172 can be combined into one electronic board or module which performs the same functions.

In the disclosed embodiment, software is resident in the electronic processor module 30 and, in particular, in the system board 184. In general, the software is used only in the initial stages of operation to initialize the system. Other software also can be resident to aid in image enhancement and zooming, for example.

The electrical shutter (described previously) is controlled by the camera controller 168 to compensate for a relatively limited range of ambient light fluctuations. To provide a greater range over which the system can automatically and dynamically adjust the brightness of the video image, the light source 92 can be switched from a manual mode to an automatic mode (e.g., by a switch on the enclosure 216).

Figure 15A:
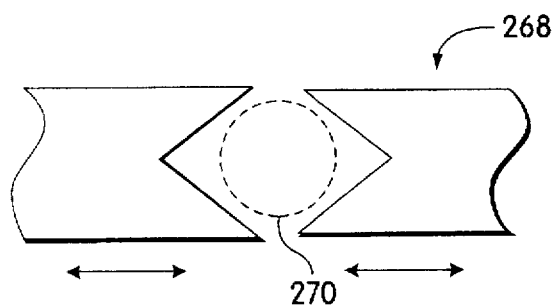
FIGS. 15A and 15B are diagrams of a controllable mechanical shutter associated with a light source of the medical video endoscope system.
Figure 15B:
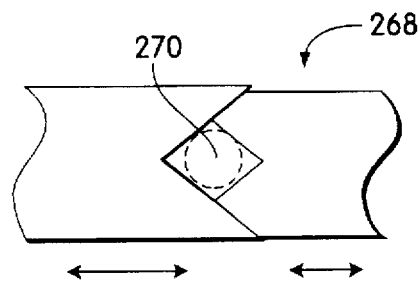

Referring to FIGS. 15A and 15B, in the manual mode, a mechanical shutter 268 associated with the light source 92 is fixed in one position until it is manually adjusted to let more or less light through an iris 270 formed by the mechanical shutter 268. The electrical shutter provides substantially all of the brightness control in the manual mode.

In the automatic mode, the mechanical shutter 268 is controlled by the camera controller 168 such that the iris 270 is automatically and dynamically adjusted. In this mode, the electrical shutter is still operating and the mechanical shutter 268 cooperates with the electrical shutter to provide an improvement in range over the manual mode of about ten-to-one or more; that is, in the automatic mode, the range of ambient light which can be compensated for generally is at least about ten times greater than in the manual mode. This improvement over the manual mode is achieved mainly because the automatic mode employs both the electrical shutter, which quickly corrects variations in the brightness of the video image but over a limited range of ambient light fluctuations, and the mechanical shutter 268, which more slowly responds to brightness variations but which compensates for a much wider range of ambient light.

In the automatic mode, as the ambient light increases, the iris 270 is narrowed automatically to allow less light to pass from the light source 92 to the endoscope 26, and, conversely, as the ambient light decreases, the iris 270 opens to allow more light to pass. The automatically and dynamically controlled iris 270 results in video images having accurate brightness and color resolution in a very wide range of ambient light levels. The automatic mode is very useful because it allows a user to concentrate primarily on the medical procedure being performed and provides a video image of appropriate brightness in a very wide range of ambient light conditions without having to manually adjust the intensity of the light from the light source 92.

Referring back to FIG. 11, a printer 210 can be connected to the camera controller 168, for example, via the buffer board 180. The printer 210 can be a commercially-available video printer, or any of a variety of other types of printers known to those of ordinary skill in the art.

The camera controller 168 can have an edge connector 212 which accepts the cable 160 (as described above with relation to FIGS. 9B and 5, cable 160 is a cable having both electrical wires and light-carrying fibers) and which provides, for example, electrical signals, optical signals, and light for illumination to the cable 160.

The power supply 182, as mentioned previously, can be a UL/CSA-registered 300 watt power supply. The isolation transformer 190 acts to isolate the ground and thus keep leakage current down to the very low levels (e.g., less than 100 microamps) required for medical applications.

The one or more monitors which display the sequentially-presented frames output by the electronic processor module 30 can use either a selection technique or a multiplexing technique. In the multiplexing technique, left and right images are displayed simultaneously on the monitor(s). The currently preferred method of display is the selection technique because it allows a viewer to realize more accurate, more realistic, higher resolution, binocular, color, real-time, stereoscopic, three-dimensional images. In the selection technique, each eye of a viewer is presented with substantially only one type of image, left or right. Other techniques are possible and are known to those of ordinary skill in the art.

Figure 12A:
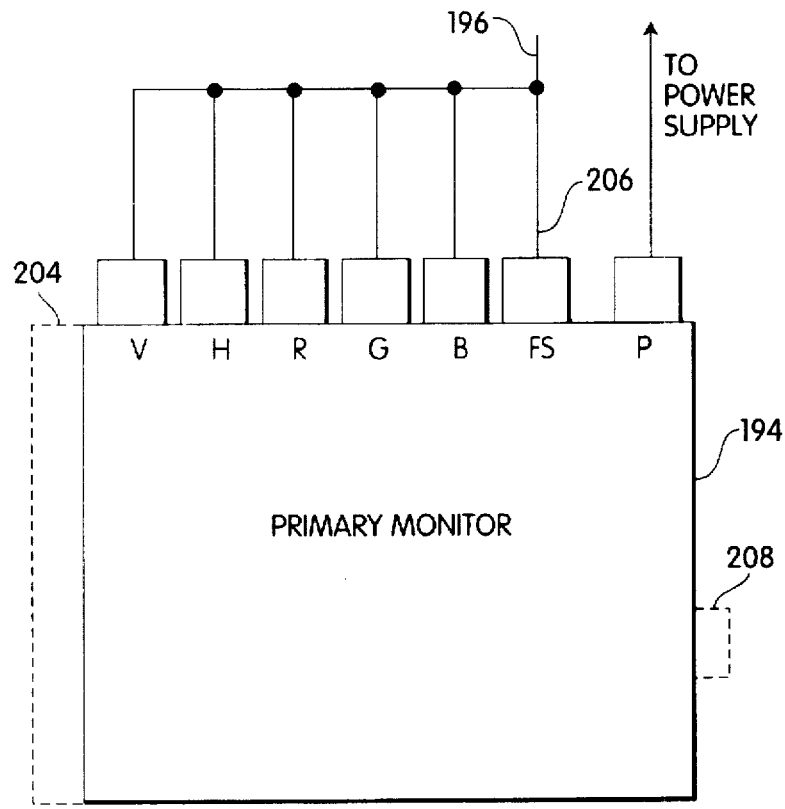
FIGS. 12A, 12B, and 12C are block diagrams of monitors of the medical video endoscope system.
Figure 12B:
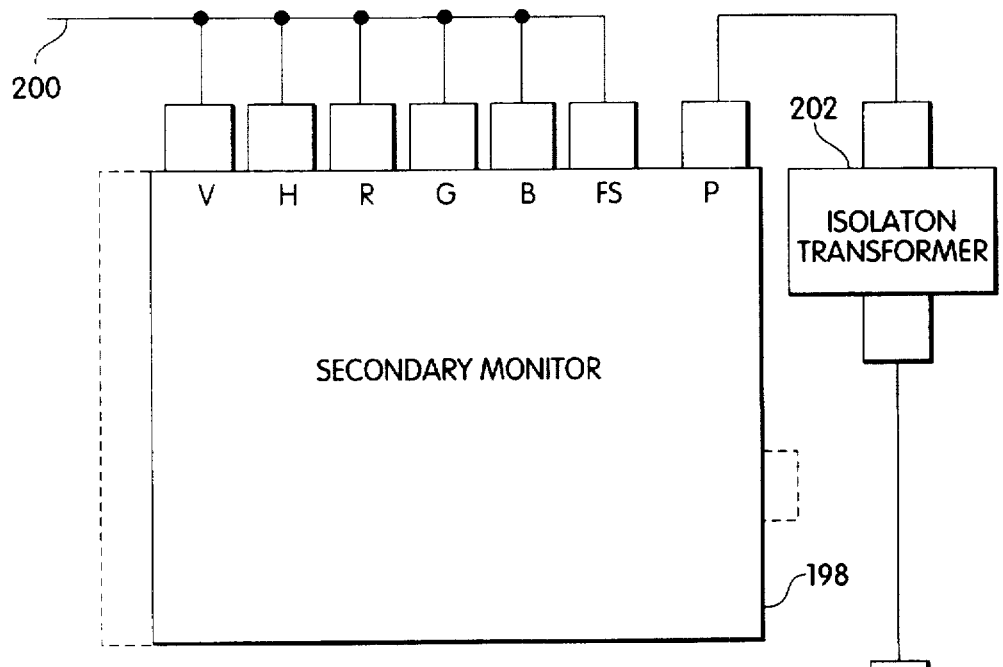
Figure 12C:
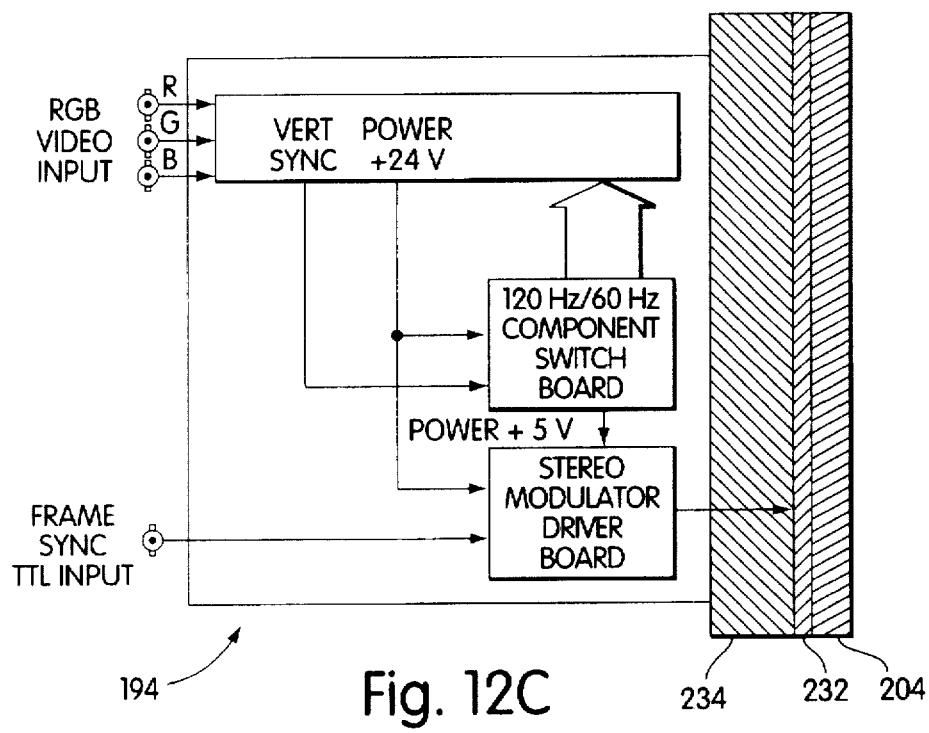

Referring to FIGS. 12A, 12B, and 12C, in the disclosed embodiment, the sequentially-presented frames output by the electronic processor module 30 on the lines 196 and 200 are provided to both the primary and secondary monitors 194, 198. Two monitors are provided to allow multiple viewers to see images of an object being viewed. For example, a primary physician standing on one side of an operating table can view images on the primary monitor 194 and an assistant standing on the other side of the operating table can view the same images on the secondary monitor 196. The primary monitor 194 typically is larger (e.g., 19 inch screen) than the secondary monitor 196 (e.g., 16 inch screen). In general, any number of monitors can be used.

While the primary monitor 194 and the secondary monitor 198 essentially are the same, in the disclosed embodiment, the secondary monitor 198 is shown connected to an isolation transformer 202 whereas the primary monitor 194 is not. The primary monitor 194, however, is connected to the isolation transformer 190 (FIG. 11), but it is just not shown explicitly in FIG. 12A. In view of the similarity between the primary and secondary monitors 194, 198, the description below will focus mainly on the primary monitor 194, but it is to be understood that the description applies also to the secondary monitor 198.

The monitor 194 can be provided in one of two configurations which are both implementations of the selection technique. The first configuration is referred to as "active screen" and the second configuration is known as "passive screen." The "active screen" configuration requires the use of "passive" eyewear (described below), and the "passive screen" configuration requires the use of "active" eyewear (also described below).

Both the "active screen" and the "passive screen" configurations achieve left and right frame separation and present each eye of a viewer with substantially only one type of image (e.g., left eye with the left image and the right eye with the right image) at a time. At the refresh rate employed, flicker (as perceived by each eye of a viewer) essentially is eliminated even though half of the time each eye of the viewer is blocked and sees substantially no image at all. The "active screen" configuration currently is preferred. A person of ordinary skill in the art will realize that other configurations besides "active screen" and "passive screen" are possible.

In the "active screen" configuration, the left and right images are alternated rapidly on the screen of the monitor 194, and a selection device is used to "separate" the images. The selection device can be a modulator 204 which is made to have a first polarization (e.g., a clockwise circular polarization) while the left image is written to the screen of the monitor 194 and a second polarization (e.g., a counter-clockwise circular polarization) while the right image is written to the screen of the monitor 194. The modulator 204 can be an active liquid crystal (LC) panel which changes the polarization characteristics of light emitted from the screen of the monitor 194 in synchronization with the image frame display rate. A sync signal 206 provided by the electronic processor module 30 (specifically, the sync board 188) on the line 196 can be used to coordinate the polarization of the modulator 204 with with the image frames. An adapter 232 (i.e., an interface connector) between the monitor 194 and the modulator 204 can be located on a bezel 234 mounted on the monitor 194 which is designed to receive the modulator 204. By using the bezel 234, electrical connections, including power, can be made automatically when the modulator 204 is mounted on the monitor 194. A suitable monitor and modulator are commercially available, for example, from Tektronix.

In the "passive screen" configuration, the left and right images are still alternated rapidly on the screen of the monitor 194, and a selection device is still used to "separate" the images. With this configuration, however, the selection device includes an IR emitter 208 which broadcasts a signal in response to the sync signal 206. "Active" eyewear (described below) receives the broadcasted signal and substantially "blackens" the appropriate lens, left or right. The emitter 208 can be approximately 4.6 inches by 2.8 inches by 1.0 inches in size, and its power requirements can be 12–18 Volts AC or DC. A suitable emitter/active eyewear product is commercially available, for example, from Stereographics or Tektronix.

The lines 196 and 200 which carry signals to the primary and secondary monitors 194, 198 from the electronic processor module 30 can have six separate wires which carry the following signals: Vertical (V), Horizontal (H), Red (R), Green (G), Blue (B), and Sync (FS).

Note that suitable monitors typically are commercially available in sizes from 16 inches to 20 inches, have prior UL an CSA approval, and have power requirements of 120 Volts AC or 240 Volts AC, at 60 Hertz. The monitors used preferably have a resolution of at least 450 lines horizontal and 470 lines vertical.

Figure 13A:
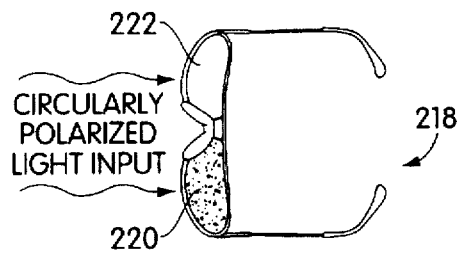
FIGS. 13A, 13B, and 13C are diagrams of viewing devices for use with the medical video endoscope system.
Figure 13B:
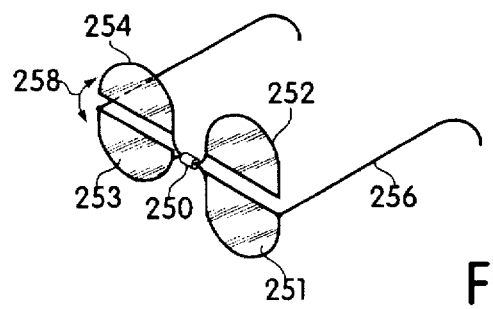
Figure 13C:
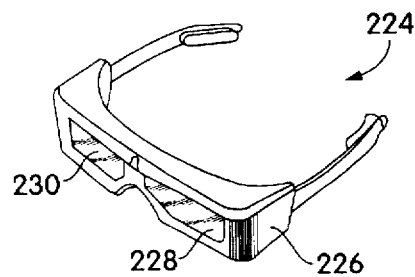

Referring to FIGS. 13A, 13B, and 13C, the viewing device can be either "active" or "passive." As mentioned previously, "passive" viewing devices are to be used with the "active screen" monitor configuration, and "active" viewing devices are for use with the "passive screen" monitor configuration.

A "passive" viewing device (FIG. 13A) is preferred (for reasons such as cost, weight, and comfort) and is typically used with the modulator 204 (i.e., in the "active screen" configuration of the monitor). The passive viewing device can be eyewear 218 (e.g., eyeglasses) having a first lens 220 with the first polarization (e.g., a clockwise circular polarization) and a second lens 222 with the second polarization (e.g., a counter-clockwise circular polarization). Other polarization schemes besides circular polarization are possible and known to one of ordinary skill in the art. When the modulator 204 is made to have the first polarization (e.g., when the left image is displayed on the screen of the monitor), a first eye of a wearer of the passive eyewear will be able to see the displayed image while a second eye of the wearer will be blocked substantially from seeing anything. Conversely, when the modulator 204 is made to have the second polarization (e.g., when the right image is displayed on the screen of the monitor), the second eye of the wearer will be able to see the displayed image while the first eye of the wearer will be blocked similarly. Suitable passive viewing devices are commercially available, for example, from Tektronix.

In one embodiment (FIG. 13B), a passive viewing device is eyewear having an integral hinge 250 connecting a flippable set of lenses 252, 254 to a conventional pair of glasses 256 having lenses 251, 253. Note that the lenses 252, 254 are not "clip-ons" but are instead an integral part of the eyewear which are connected to the glasses 256 by the integral hinge 250. Typically, a user is provided with glasses 256 having lenses 251, 253 which are plano (i.e., clear and non-prescription), and the user has the clear lenses replaced with prescription lenses, if necessary, by an optician. A user who does not need corrective lenses can leave the clear lenses in the glasses 256. The flippable set of lenses 252, 254 connected to the glasses 256 by the integral hinge 250 can have, respectively, the first polarization (e.g., a clockwise circular polarization) and the second polarization (e.g., a counter-clockwise circular polarization). The lenses 252, 254 can be flipped down or up to be placed in or out, respectively, of the viewer's line of vision, as indicated by an arrow 258. When the viewer desires to view three-dimensional images having stereoscopic depth on the monitor(s), the viewer flips the lenses 252, 254 down to place them in his or her line of vision. Conversely, the viewer flips up the lenses 252, 254 to remove the lenses from his or her line of vision. Note that the positioning of the lenses 252, 254 can be performed by a person other than the viewer. For example, if the viewer is scrubbed and non-contaminated (e.g., a gowned and gloved surgeon), a helper (e.g., a nurse) can flip the lenses 252, 254 up and down and thus allow the viewer to remain uncontaminated.

Another embodiment of a passive viewing device is a pair of safety goggles which can be placed over a user's existing glasses. The lenses of the goggles will have the first and second polarization, respectively. Similar to the description in the previous paragraph, the goggles can be placed on and taken off of a viewer by a person other than the viewer. For example, a nurse can put the goggles on, and take them off of, a surgeon prepared to perform a surgical procedure. Alternatively, a surgeon can put the goggles on prior to preparing for the surgical procedure without the aid of the nurse and leave them on throughout the preparation process and the surgery.

Other forms which a passive viewing device can take are known to those of ordinary skill in the art.

An "active" viewing device (FIG. 13C) is typically used when the "passive screen" monitor configuration is employed. The active viewing device can be "shuttering" eyewear 224 (e.g., glasses) which "blink" in synchronization with the sync signal 206 broadcast by the emitter 208. The eyewear 224 typically has an IR detector mounted on or in the frame 226 of the eyewear, and liquid crystal lenses 228, 230 which polarize (e.g., "blacken") in response to the sync signal 206 to provide a first eye of a wearer with substantially only the left images displayed on the screen of the monitor and a second of the wearer with substantially only the right images displayed on the screen. The lenses can be surface mode orthochromatic liquid crystal devices. Power can be supplied by two 3 Volt lithium/manganese dioxide batteries located, for example, in the frame 226. Suitable active viewing devices are commercially available, for example, from Tektronix or Stereographics.

As with the passive viewing device, an active viewing device can take a variety of forms as will be appreciated by those of ordinary skill in the art. Regardless of the type and form of viewing device employed, the viewing device preferably meets all applicable safety requirements such as dictated by the Occupational Safety and Health Administration (OSHA), hospitals, and other authorities.

Note that in both the passive and active configurations of the viewing device, the lenses of the viewing device (e.g., 220, 222, 228, and 230) typically are not capable of becoming completely blocked or opaque but instead typically have an extinction of about 80%. The "blocked" eye thus typically can see something but not enough to destroy or significantly degrade the three-dimensional effect. Consequently, in general, the higher the extinction associated with the viewing device, the more completely the eye is blocked, for example, an extinction of 90% provides more "blocking" than an extinction of 80%.

As indicated previously, the transmission channel 28 can couple the stereoscopic endoscope 26 directly to the viewing device 34 of FIG. 1 which can be, for example, a video projector system including two video projectors for projecting, respectively, left and right polarized images onto a screen for viewing with polarized eyewear, or a headset for providing left video images directly to the left eye of a viewer and right video images directly to the right eye of the viewer. In either configuration, the electronic processor module 30 and the monitor 32 (e.g., the monitors of FIGS. 12A, 12B, and 12C) are bypassed, but the light source 92 and the image sensor control module 50 typically continue to operate and perform all of their functions.

Referring to FIG. 14, a headset 260 can include two display devices 262, 264 mounted to place each display device directly in front of each eye of a wearer. Each eye thus sees only one "type" of image. For example, the display device 262 can directly receive only the signals 58 from the endoscope 26, and the other display device 264 can directly receive only the signals 60. Consequently, the display device 262 displays only left video images which only the left eye of the wearer will see and the other display device 264 displays only the right video images which only the right eye will see. The transmission channel 28 can be a cable 266 which provides the signals 58, 60 to the headset 260 from the endoscope 26.

A person wearing the headset 260 will be able to look directly at the display devices 262, 264 to view stereoscopic images of an object, or look away from the display devices 262, 264 to view the surroundings. A surgeon will find the headset 260 especially useful during surgery because during surgery, the surgeon will be able to look directly at the instruments he is manipulating with his hands, and will also be able to switch easily and quickly between looking at the devices 262, 264 and looking at the patient, thus allowing the surgeon to be completely aware at all times of the surroundings and the surgical procedure being performed.

Figure 17:
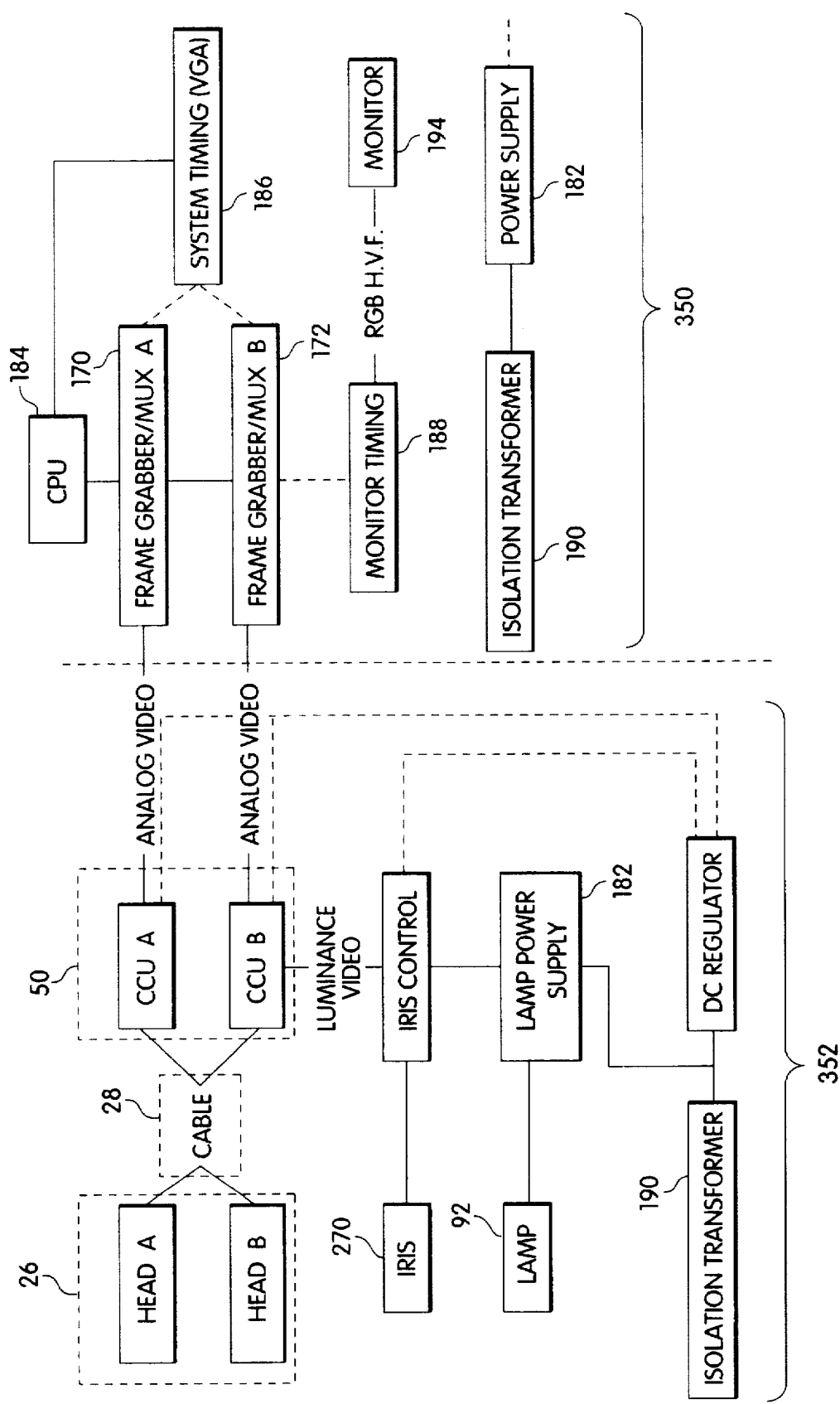
FIG. 17 is a block diagram of a three-dimensional medical video endoscope system according to the invention.

Referring to FIG. 17, a three-dimensional medical video endoscope system according to the invention has been shown and described herein as including a stereoscopic endoscope 26 coupled by a cable 28 to electronic processing components which process and display a stereoscopic image. The stereoscopic endoscope includes two image sensing devices such as CCD cameras (labeled HEAD A and HEAD B in FIG. 17). A cable couples the three-dimensional endoscope to the electronic processing components. The electronic processing components generally can be divided into a signal processing unit (SPU) 350 and an image control unit (ICU) 352. The SPU 350 includes the motion video boards 170 and 172 (e.g., shown in FIG. 11), the central processor 184, the VGA board 186, the sync board 188, and the power supply 182. The ICU 352 includes the light source 92 and the iris controller.

Figure 18:
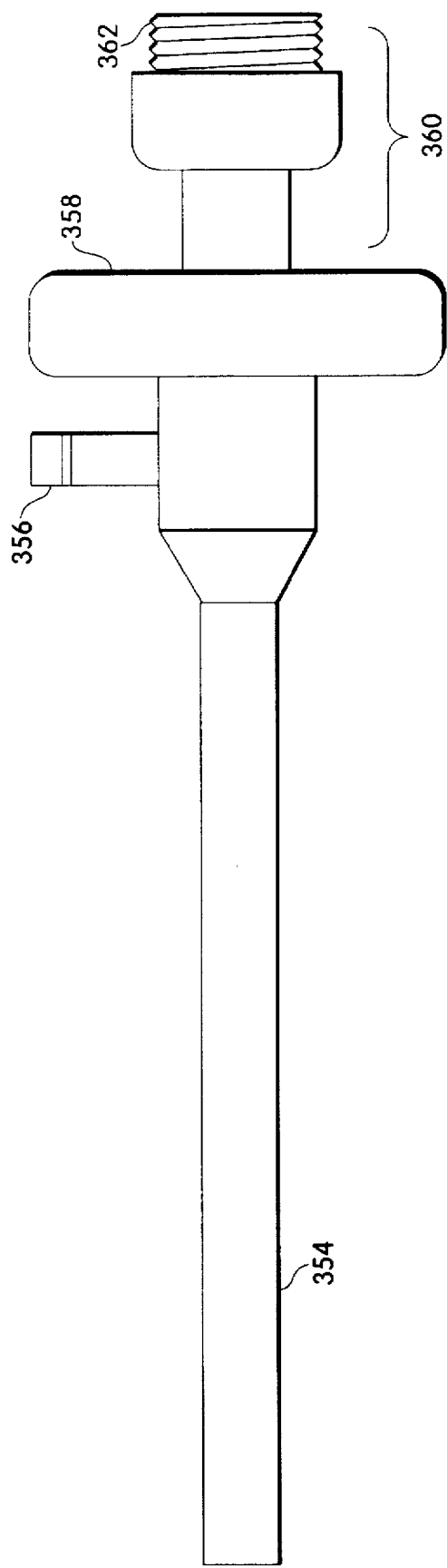
FIG. 18 shows a conventional two-dimensional endoscope.

In some embodiments of the invention, the stereoscopic endoscope 26 can be replaced by a conventional two-dimensional endoscope. In these alternative embodiments, the three-dimensional medical video endoscope system according to the invention creates a two-dimensional video image of the object(s) being viewed by the conventional two-dimensional video endoscope. Because the inventive three-dimensional medical video endoscope system can be used with existing, conventional endoscopes, the inventive system is versatile and cost-effective. As shown in FIG. 18, a conventional two-dimensional endoscope can have a barrel portion 354, a fitting 356 for connecting to a light source, and an eyepiece 358. To the eyepiece 358 of the conventional two-dimensional endoscope is connected a camera coupler 360 which adapts the eyepiece 358 to allow connection of the conventional two-dimensional endoscope to a video system. The camera coupler 360 is a standard "C" mount endoscope coupler which has a threaded portion 362. A camera head according to the invention is provided which connects to the threaded portion 362 of the camera coupler 360 to interface the conventional two-dimensional endoscope to a three-dimensional medical video endoscope system according to the invention such as the one of FIG. 17. Referring to FIG. 17, in these alternative embodiments, the stereoscopic endoscope 26 is replaced by the coupled combination of the conventional two-dimensional endoscope of FIG. 18 and the inventive camera head. The cable 28 couples the inventive camera head to the CCUs 50.

Figure 19A:
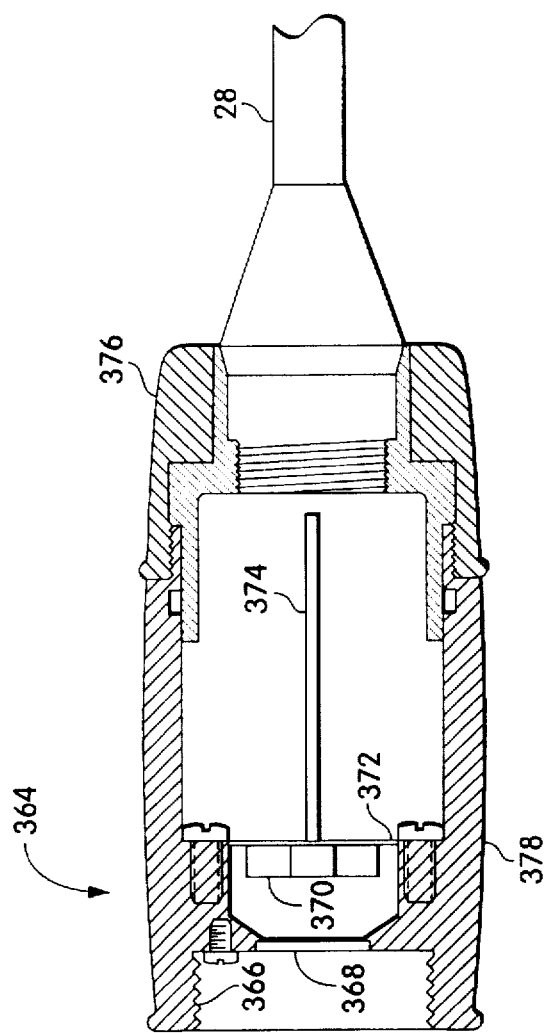
FIGS. 19A and 19B are physical and functional diagrams, respectively, of a camera head for coupling a conventional two-dimensional endoscope (such as shown in FIG. 18) to a three-dimensional medical video endoscope system according to the invention (such as shown in FIGS. 1, 10, 11, and 17).

Referring to FIG. 19A, the inventive camera head 364 includes a female threaded portion 366 for receiving the threaded portion 362 of the camera coupler 360 shown in FIG. 18. Images from the conventional two-dimensional endoscope travel through a window 368 in the camera head 364 and onto a CCD camera 370 which is mounted on a first printed circuit (PC) board 372. To the first PC board 372 is connected a second PC board 374. The first and second PC boards 372 and 374 together include the camera head driver electronics which will be described in detail later with reference to FIG. 19B. In general, the driver electronics generate two signals which can be used to drive a three-dimensional medical video endoscope system according to the invention. The camera head 364 has a ringnut 376 for removably coupling the video cable 28 which connects to the CCUs (FIG. 17). In the disclosed embodiment, the body 378 of the camera head 364 is made of aluminum.

Figure 19B:
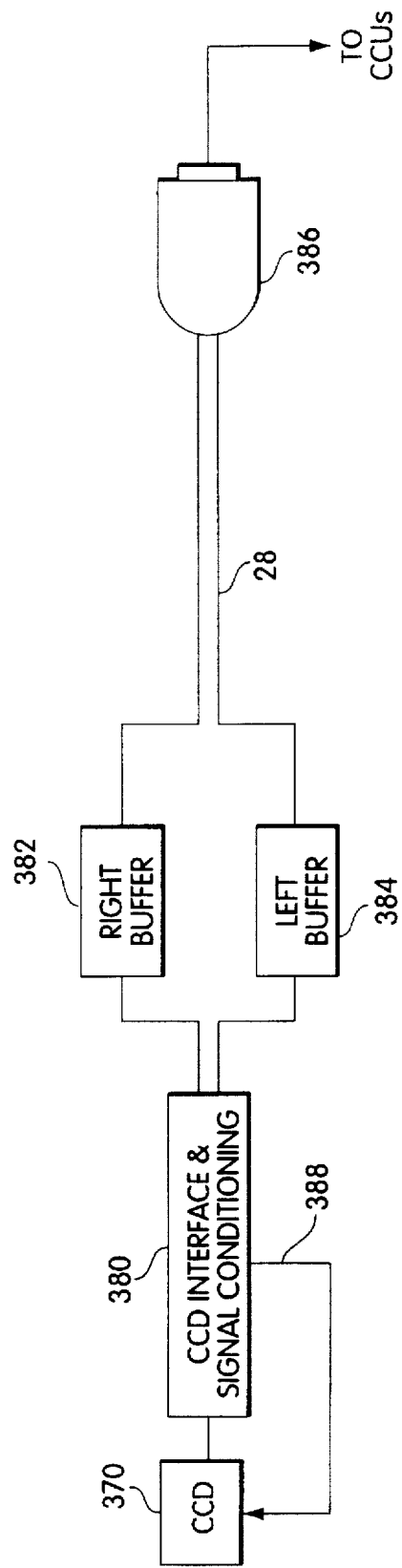

Referring to FIG. 19B, the camera head driver electronics include the CCD camera 370, a CCD interface and signal conditioning circuit 380, a right buffer 382, and a left buffer 384. The two buffers 382 and 384 are coupled to the CCUs (FIG. 17) by the cable 28 which terminates in a connector 386. The circuit 380 receives the output signal from the CCD 370 and provides a correction signal 388 to the CCD 370. The circuit 380 also processes the output signal from the CCD 370 and provides one signal to the right buffer 382 and another signal to the left buffer 384. The two signals provided to the buffers generally are the same; two "channels" must be created by the camera head driver electronics so that the three-dimensional medical video endoscope system according to the invention operates properly. Having created the two (left and right) signals from the single CCD output signal, the two signals can be provided to the three-dimensional system and it will operate as described herein except that the left and right channels will process essentially the same signals and that the ultimate video image created will be two-dimensional instead of stereoscopic.

Other modifications and implementations will occur to those skilled in the art without departing from the spirit and the scope of the invention as claimed. Accordingly, the invention is to be defined not by the preceding illustrative description, but by the following claims.

What is claimed is:

1. A medical video endoscope system comprising:
   (a) a stereoscopic endoscope comprising a handle portion (68), a tubular barrel portion (66), and a light-sensing system, said tubular barrel portion containing an objective lens system (36) for generating left and right optical images of an object viewed by said medical video endoscope system, and said light-sensing system including means for alternately sensing said left and right optical images and converting said sensed left and right optical images to left and right video image signals respectively; and
   (b) a tubular sheath assembly (300) having a longitudinal axis and surrounding and extending lengthwise of and parallel to said barrel portion of said endoscope, said tubular sheath assembly (i) being rotatable relative to said barrel portion, (ii) including a distal tip portion (310) having a front face (304) that extends at an acute angle to said longitudinal axis, and (iii) containing optical means (320, 322, 324, 326) for directing optical images from the direction in which said front face of the angled distal tip portion is pointed to said objective lens system, whereby rotation of said sheath assembly relative to said barrel portion causes changes in the direction in which said front face of said distal tip portion is pointed and thus allows viewing direction changes in the stereoscopic endoscope viewing of said object in response to rotation of said sheath assembly relative to said barrel portion.

2. An endoscope system according to claim 1 wherein said optical means includes a plurality of lenses that are disposed to transmit images to said objective lens system.

3. An endoscope system according to claim 1 wherein said optical means includes at least a negative lens and a prism that are disposed to transmit images to said objective lens system.

4. An endoscope system according to claim 3 wherein said optical means includes a front negative lens (320), a prism (322), and a rear positive lens (324).

5. An endoscope system according to claim 4 wherein said front negative lens (320), said prism (322), and said rear positive lens (324) are disposed at said tip portion (310) of said sheath assembly.

6. An endoscope system according to claim 1 wherein said handle portion (68) includes a nose cone (84), and said barrel portion (66) is attached to said nose cone.

7. An endoscope system according to claim 6 wherein said sheath assembly includes a nose cone extension (306) that is coupled to said nose cone (84).

8. An endoscope system according to claim 7 further including a latch means (312) for releasably and mechanically coupling said nose cone extension to said nose cone.

9. An endoscope system according to claim 1 further including a latch means (312) for releasably coupling said sheath assembly to said handle portion.

10. An endoscope system according to claim 1 wherein said sheath assembly includes an inner tube (302) and an outer tube (318) that is fixed with respect to said inner tube, and means (316) interposed between said inner and outer tubes for conducting light to illuminate said object.

11. An endoscope system according to claim 10 wherein said optical means includes a plurality of lenses that are disposed to transmit images to said objective lens system, and at least one of said plurality of lenses is disposed in said outer tube in front of said inner tube and at least another of said plurality of lenses is disposed in said inner tube.

12. An endoscope system according to claim 11 wherein said optical means includes a prism, and said prism is disposed in said outer tube in front of said inner tube.

13. An endoscope according to claim 10 wherein said means (316) for conducting light to illuminate said object comprises optical fibers.

14. An endoscope according to claim 1 wherein said sheath assembly includes optical illumination fibers (316) for transmitting light to the said distal tip portion of said sheath assembly.

15. An endoscope system according to claim 1 wherein said barrel portion and said handle portion are detachable coupled to one another so as to allow removal and cleaning of said barrel portion.

16. A medical video endoscope system comprising:
(a) a stereoscopic endoscope having a handle portion (68), a barrel portion (66), said barrel portion having a distal end and a proximate end, and an objective lens system (36) mounted in said distal end of said barrel portion for generating left and right optical images of an object viewed by said medical video endoscope system, said endoscope also including a light-sensing system for alternately sensing said left optical images and right optical images, and converting said sensed left and right optical images to left and right video image signals respectively; and
(b) a sheath assembly (300) having a longitudinal axis and surrounding and extending lengthwise of and parallel to said barrel portion of said endoscope, said sheath assembly being rotatable relative to said barrel portion, and said sheath assembly including an angled front face and optics for receiving optical images from the direction in which said front face of the angled distal tip is pointed and transmitting said optical images to said objective lens system, whereby rotation of said sheath assembly causes changes in the direction in which said angled front face is pointed and thus allows angular endoscope viewing of said object according to rotation of said sheath assembly relative to said barrel portion.

17. An endoscope system according to claim 16 further including a sheath latch means for releasably and mechanically coupling said sheath assembly to said endoscope.

18. An endoscope system according to claim 16 wherein said sheath assembly includes a light guide adapter fitting (314) for receiving light from a light source, and optical illumination fibers (316) for transmitting light from said light guide adapter to the said distal end of said sheath assembly.

19. An endoscope system according to claim 16 wherein said sheath assembly comprises first and second concentric tubes, and means disposed between said first and second tubes for transmitting light to the distal end of said sheath assembly so as to illuminate said object.

20. An endoscope system according to claim 16 wherein said barrel portion contains an objective lens and a relay lens.

21. An endoscope system according to claim 16 wherein said handle portion contains said light-sensing system.

22. An endoscope system according to claim 16 wherein said barrel portion contains said light-sensing system.

23. A medical video endoscope system comprising:
(a) an endoscope having a handle portion (68) and a tubular barrel portion (66), said tubular barrel portion including an objective lens system (36) for generating optical images of an object viewed by said medical video endoscope system, said endoscope also including a light-sensing system for sensing said optical images and converting said sensed optical images to video image signals; and
(b) a tubular sheath assembly (300) having a longitudinal axis and surrounding and extending lengthwise of and parallel to said barrel portion of said endoscope, said tubular sheath assembly (i) being rotatable relative to said barrel portion, (ii) including a distal tip portion (310) having a front face (304) that extends at an acute angle to the longitudinal axis of said sheath assembly, and (iii) optical means (320, 322, 324, 326) for directing optical images from the direction in which said front face of the angled distal tip portion is pointed to said objective lens system, whereby rotation of said sheath assembly relative to said barrel portion causes changes in the direction in which said front face of said distal tip portion is pointed and thus allows viewing direction changes in the endoscope viewing of said object in response to rotation of said sheath assembly relative to said barrel portion.

24. An endoscope system according to claim 23 wherein said optical means includes lenses that are disposed to transmit images to said objective lens system.

25. An endoscope system according to claim 23 wherein sheath includes a front negative lens and a prism for directing images to said objective lens system.

26. An endoscope system according to claim 23 wherein sheath includes a front negative lens (320), a prism (322), and a rear positive lens (324).

27. An endoscope system according to claim 26 wherein said front negative lens (320), prism (322), and rear positive lens (324) are disposed at said tip portion of said sheath assembly.

28. An endoscope system according to claim 26 wherein said negative lens is located in front of said prism.

29. An endoscope system according to claim 23 wherein said barrel portion is separable from said handle portion, so that a different barrel portion may be attached to said handle portion.

30. A medical video endoscope system comprising:
(a) an endoscope having a handle portion (68) and a tubular barrel portion (66), said tubular barrel portion including an objective lens system (36) for generating left and right optical images of an object viewed by said medical video endoscope system;
(b) a tubular sheath assembly (300) having a longitudinal axis and surrounding and extending lengthwise of and parallel to said barrel portion of said endoscope, said tubular sheath assembly (i) being rotatable relative to said barrel portion, (ii) including a distal tip portion (310) having a front face (304) that extends at an acute angle to said longitudinal axis, and (iii) containing optical means (320, 322, 324, 326) for directing optical images from the direction in which said front face of the angled distal tip portion is pointed to said objective lens system, whereby rotation of said sheath assembly relative to said barrel portion causes changes in the direction in which said front face of said distal tip portion is pointed and thus allows viewing direction changes in the stereoscopic endoscope viewing of said object in response to rotation of said sheath assembly relative to said barrel portion;
(c) a light-sensing module comprising image-sensing means for sensing said left and right optical images and for producing left and right electrical signals in response to said sensed left and right optical images respectively;
(d) processing electronics for creating left and right video image signals in response to said left and right electrical signals respectively;
(e) means for controlling said image-sensing means;
(f) means for receiving said left and right video image signals and for processing each of said left and right video image signals at a first rate to generate time-multiplexed left and right video image signals, each time-multiplexed video image signal being representative of an image frame having a predetermined number of unique horizontal video lines, and said time-multiplexed video image signals being suitable for transmission at a second rate which is approximately twice said first rate; and
(g) a viewing system (31) including a video monitor (32) for receiving said time-multiplexed video image signals at said second rate and displaying left and right video images based on said time-multiplexed video image signals, each video image having said predetermined number of unique horizontal video lines.

31. A medical video endoscope system comprising:
(a) a stereoscopic endoscope having a handle portion (68), a barrel portion (66), said barrel portion having a distal end and a proximate end, and an objective lens system (36) mounted in said distal end of said barrel portion for generating left and right optical images of an object viewed by said medical video endoscope system;
(b) a sheath assembly (300) having a longitudinal axis and surrounding and extending lengthwise of and parallel to said barrel portion of said endoscope, said sheath assembly being rotatable relative to said barrel portion and including an angled front face and optics for receiving optical images from the direction in which said front face of the angled distal tip is pointed and transmitting said optical images to said objective lens system, whereby rotation of said sheath assembly causes changes in the direction in which said angled front face is pointed and thus allows angular endoscope viewing of said object according to rotation of said sheath assembly relative to said barrel portion;
(c) a light-sensing module comprising image-sensing means for alternately sensing said left and right optical images and for producing left and right electrical signals in response to said sensed left and right optical images respectively;
(d) processing electronics for creating left and right video image signals in response to said left and right electrical signals respectively;
(e) means for controlling said image-sensing means;
(f) means for receiving said left and right video image signals and for processing each of said left and right video image signals at a first rate to generate time-multiplexed left and right video image signals, each time-multiplexed video image signal being representative of an image frame having a predetermined number of unique horizontal video lines, and said time-multiplexed video image signals being suitable for transmission at a second rate which is approximately twice said first rate; and
(g) a viewing system (31) including a video monitor (32) for receiving said time-multiplexed video image signals at said second rate and displaying left and right video images based on said time-multiplexed video image signals, each video image having said predetermined number of unique horizontal video lines.

* * * * *

UNITED STATES PATENT AND TRADEMARK OFFICE
CERTIFICATE OF CORRECTION

PATENT NO.   : 5,751,341
DATED        : May 12, 1998
INVENTOR(S)  : Christopher R. Chaleki et al It is certified that error appears in the above-indentified patent and that said Letters Patent is hereby corrected as shown below:

Claim 25, column 23, line 10, delete the word "sheath" and insert the phrase -- said sheath assembly --; and Claim 26, column 23, line 13, delete the word "sheath" and insert the phrase -- said sheath assembly --.

Signed and Sealed this

Eighteenth Day of August, 1998

Attest:

BRUCE LEHMAN

*Attesting Officer*      *Commissioner of Patents and Trademarks*